(12) United States Patent
Pratt et al.

(10) Patent No.: US 7,056,355 B2
(45) Date of Patent: Jun. 6, 2006

(54) HAIR DYE COMPOSITION AND DYEING METHOD

(75) Inventors: Dominic Pratt, Darmstadt (DE); Toshio Kawagishi, Minamiashigara (DE)

(73) Assignees: Kao Corporation, Tokyo (JP); Fuji Photo Film Co., Ltd., Minamiashigara (JP)

( * ) Notice: Subject to any disclaimer, the term of this patent is extended or adjusted under 35 U.S.C. 154(b) by 271 days.

(21) Appl. No.: 10/661,609

(22) Filed: Sep. 15, 2003

(65) Prior Publication Data
US 2005/0015896 A1    Jan. 27, 2005

(30) Foreign Application Priority Data
Sep. 16, 2002   (EP)   ................................. 02020528

(51) Int. Cl.
*A61K 7/13*   (2006.01)
(52) U.S. Cl. .................. 8/405; 8/407; 8/437; 8/451; 8/463; 8/466; 8/570; 8/573; 8/574; 548/400; 546/1
(58) Field of Classification Search ............... 8/405, 8/407, 437, 451, 463, 466, 570, 573, 574; 548/400; 546/1
See application file for complete search history.

(56) References Cited

U.S. PATENT DOCUMENTS 3,148,179 A * 9/1964 Carboni .................. 534/741
3,164,522 A * 1/1965 Charle et al. ............... 8/424
5,889,163 A   3/1999 Takeuchi et al. .......... 534/580
6,027,537 A * 2/2000 Leduc et al. ................ 8/405

FOREIGN PATENT DOCUMENTS

| DE | 135016 | 8/1901 |
| DE | 100 28 686 | 12/2001 |
| GB | 844873 | 8/1960 |
| JP | 6-271435 | 9/1994 |

OTHER PUBLICATIONS

Patent Abstracts of Japan, JP 01-271468, Oct. 30, 1989.

* cited by examiner

*Primary Examiner*—Eisa Elhilo
(74) *Attorney, Agent, or Firm*—Oblon, Spivak, McClelland, Maier & Neustadt, P.C.

(57) ABSTRACT

The present invention is directed to a hair dyeing composition containing a dissociative azo dye of the following general formula (1)

$$A-N=N-B \qquad (1)$$

wherein "A" represents a phenyl or naphthyl group which may be substitued; "B" represents an atomic group containing a dissociative proton, with the proviso "A" and "B" are free of sulfo, carboxyl and quaternary ammonium groups. Additionally, the present invention describes a method of dyeing human or animal hair by using such a dye and the use of this direct azo dye for dyeing human or animal hair. The use of this direct azo dye can impart the hair with an extremely vivid color and has less color fading over time.

14 Claims, No Drawings

HAIR DYE COMPOSITION AND DYEING METHOD

FIELD OF THE INVENTION

The present invention relates to a hair dye composition containing azo dyes.

BACKGROUND OF THE INVENTION

Hair dyes can be classified by the dye to be used or by whether they have any bleaching action on melanin. Typical examples include a two-part permanent hair dye composed of a first part containing an alkaline agent, an oxidation dye and optionally a direct dye such as a nitro dye and a second part containing an oxidizing agent; and a one-part semi-permanent hair dye containing an organic acid or an alkaline agent, and at least one direct dye such as an acid dye, a basic dye or a nitro dye.

The above-described permanent hair dye is however accompanied with the drawbacks that the colour tone imparted by an oxidation dye is not so vivid and that the colour of the hair dyed with a vivid-colour producing nitro dye ordinarily employed as a direct dye markedly fades over time and becomes dull quickly, even if the colour tone immediately after dyeing is very vivid (Japanese Patent Application Laid-Open (Kokai) No. Hei 6-271435).

It is common practice to combine direct dyes and oxidative dyes in permanent products to provide more vivid colour; however currently available direct dyes do not usually perform satisfactorily. The number of direct dyestuff that can be used in combination with oxidative dyes is limited by the necessity that they must be stable to the alkaline peroxide during the dyeing process.

A variety of cationic direct dyes and nitro dyes have been used in permanent hair dye products to add brilliance and vividness to shades. However, in both cases the colour fades very quickly due to the loss of the direct dye from washing and exposure to light, especially on damaged or porous hair.

SUMMARY OF THE INVENTION

In one aspect of the present invention, there is thus provided a hair dyeing composition containing a dissociative azo dye represented by the following general formula (1):

A-N=N-B  (1)

wherein "A" represents a phenyl or naphthyl group which may be substitued; "B" represents an atomic group containing a dissociative proton, with the proviso "A" and "B" are free of sulfo, carboxyl and quaternary ammonium groups.

DETAILED DESCRIPTION OF THE INVENTION

All publications cited herein are hereby incorporated by reference.

The present invention relates to a hair dye composition containing as a direct dye a dissociative phenyl azo dye or naphthyl azo dye which can strongly impart the hair with a vivid colour without decomposition of the dye upon hair dyeing, has excellent resistance to fading from light, washing, perspiration, friction and heat. The dye is stable in alkaline conditions and stable against an oxidizing agent, has high hair dyeing power and shows less colour fading over time.

The present invention also relates to a hair dyeing method by applying the above mentioned azo dye to the hair.

The present inventors have found that dissociative phenyl azo dyes or naphthyl azo dyes of the general structure (1) below and the resulting dyeing composition can strongly impart the hair with a vivid colour selected from a wide range of different colours without decomposition of the dye upon hair dyeing, and exhibits excellent resistance to fading from light, washing, perspiration, friction and heat.

The phenyl or naphthyl group represented by "A" and atomic group represented by "B" in formula (1) do not contain any of carboxy, sulfo and quaternary ammonium group. The carboxy or sulfo group herein includes, in addition to the acid type groups, neutral type groups such as —COONa or —SO$_3$Na. In other words, azo dye (1) contains neither the acid or neutral type carboxy or sulfo group nor quaternary ammonium group, and is neither anionic nor cationic.

The number of carbon atoms in the phenyl or naphthyl group represented by "A" including optional substituents on the phenyl or naphthyl group is preferably 6 to 20, more preferably 6 to 10.

The phenyl or naphthyl group represented by "A" is preferably derived from a diazo component that per se is known in the art.

Herein, the diazo component means a partial structure introduced by converting an aromatic compound with a substituent amino group to a diazo compound and allowing the resulting diazo compound to be subjected along with a coupler in a diazo-coupling reaction, which belongs to a concept commonly used in the field of azo dyes.

In other words, the diazo component means a substituent prepared by eliminating an amino group from an amino-substituted aromatic compound possibly subjected to a diazo reaction, to render a resulting product that is a monovalent group.

In general formula (1), the phenyl or naphthyl group represented by "A" may contain a substituent and in that case, the substituent includes for example a halogen atom, cyclic, straight-chain or branched-chain alkyl group (including cycloalkyl group), cyclic, straight-chain or branched-chain alkenyl group (including cycloalkenyl group), alkynyl group, aryl group, hetero-ring group, cyano group, hydroxy group, nitro group, alkoxy group, aryloxy group, silyloxy group, hetero-ring oxy group, acyloxy group, carbamoyloxy group, alkoxycarbonyloxy group, aryloxycarbonyloxy, amino group (including anilino group), acylamino group, aminocarbonylamino group, alkoxycarbonylamino group, aryloxycarbonylamino group, sulfamoylamino group, alkylsulfonylamino group, arylsulfonylamino group, mercapto group, alkylthio group, arylthio group, hetero-ring thio group, sulfamoyl group, alkylsulfinyl group, arylsulfinyl group, alkylsulfonyl group, arylsulfonyl group, acyl group, alkoxycarbonyl group, aryloxycarbonyl group, carbamoyl group, arylazo group, hetero-ring azo group, imido group, phosphino group, phosphinyl group, phosphinyloxy group, phosphinylamino group, and silyl group. More specifically, the substituent includes for example a halogen atom (for example, fluorine atom, chlorine atom, bromine atom, iodine atom), alkyl group (linear or branched or cyclic alkyl group with one to 10 carbon atoms, preferably one to 6 carbon atoms, for example, methyl, ethyl, n-propyl, isopropyl, t-butyl, n-octyl, 2-chloroethyl, 2-cyanoethyl, 2-ethylhexyl, cyclopropyl, cyclopentyl), alkenyl group (linear or branched or cyclic alkenyl group with 2 to 10 carbon atoms, preferably 2 to 6 carbon atoms, for example, vinyl, allyl, prenyl, cyclopenten-1-yl), alkynyl group (alkynyl group with 2 to 10 carbon atoms, preferably 2 to 6 carbon atoms, for example, ethynyl, propargyl), aryl group (aryl group with 6 to 12 carbon atoms, preferably 6 to 8 carbon atoms, for example, phenyl, p-tolyl, naphthyl, 3-chlorophenyl, 2-aminophenyl), hetero-ring group (monovalent group with one to 12 carbon atoms, preferably 2 to 6 carbon atoms, which is recovered by eliminating one hydrogen atom from an aromatic or non-aromatic hetero-ring compound, 5-membered or 6-membered; for example, 1-pyrazolyl, 1-imidazolyl, 2-furyl, 2-thienyl, 4-pyrimidinyl, 2-benzothiazolyl), cyano group, hydroxy group, nitro group, alkoxy group (linear or branched or cyclic alkoxy group with one to 10 carbon atoms, preferably one to 6 carbon atoms, for example, methoxy, ethoxy, isopropoxy, t-butoxy, cyclopentyloxy, 2-buten-1-yloxy, 2-methoxyethoxy), aryloxy group (aryloxy group with 6 to 12 carbon atoms, preferably 6 to 8 carbon atoms, for example, phenoxy, 2-methylphenoxy, 4-t-butylphenoxy, 3-nitrophenoxy), silyloxy group (silyloxy group with 3 to 10 carbon atoms, preferably 3 to 6 carbon atoms, for example, trimethylsilyloxy, t-butyldimethylsilyloxy), hetero-ring oxy group (hetero-ring oxy group with one to 12 carbon atoms, preferably 2 to 6 carbon atoms, for example, 1-phenyltetrazole-5-oxy, 2-tetrahydropyranyloxy), acyloxy group (acyloxy group with one to 12 carbon atoms, preferably one to 8 carbon atoms, for example, formyloxy group, acetyloxy, pivaloyloxy, benzoyloxy, p-methoxyphenylcarbonyloxy), carbamoyloxy group (carbamoyloxy group with one to 10 carbon atoms, preferably one to 6 carbon atoms, for example, N,N-dimethylcarbamoyloxy, N,N-diethylcarbamoyloxy, morpholinocarbonyloxy, N-n-octylcarbamoyloxy), alkoxycarbonyloxy group (alkoxycarbonyloxy group with 2 to 10 carbon atoms, preferably 2 to 6 carbon atoms, for example, methoxycarbonyloxy, ethoxycarbonyloxy, t-butoxycarbonyloxy, n-octyloxycarbonyloxy), aryloxycarbonyloxy group (aryloxycarbonyloxy group with 7 to 12 carbon atoms, preferably 7 to 10 carbon atoms, for example, phenoxycarbonyloxy, p-methoxyphenoxycarbonyloxy), amino group (amino group, alkylamino group with one to 10 carbon atoms, preferably one to 6 carbon atoms, anilino group with 6 to 12 carbon atoms, preferably 6 to 8 carbon atoms, or hetero-ring amino group with one to 12 carbon atoms, preferably 2 to 6 carbon atoms, including for example amino, methylamino, dimethylamino, anilino, N-methyl-anilino, diphenylamino, imidazol-2-ylamino, pyrazol-3-ylamino), acylamino group (alkylcarbonylamino group with one to 10 carbon atoms, preferably one to 6 carbon atoms, arylcarbonylamino group with 6 to 12 carbon atoms, preferably 6 to 8 carbon atoms, or hetero-ring carbonylamino group with 2 to 12 carbon atoms, preferably 2 to 6 carbon atoms, including for example formylamino, acetylamino, pivaloylamino, benzoylamino, pyridine-4-carbonylamino, thiophene-2-carbonylamino), aminocarbonylamino group (aminocarbonylamino with one to 12 carbon atoms, preferably one to 6 carbon atoms, for example, carbamoylamino, N,N-dimethylaminocarbonylamino, N,N-diethylaminocarbonylamino, morpholin-4-ylcarbonylamino), alkoxycarbonylamino group (alkoxycarbonylamino group with 2 to 10 carbon atoms, preferably 2 to 6 carbon atoms, for example, methoxycarbonylamino, ethoxycarbonylamino, t-butoxycarbonylamino), aryloxycarbonylamino group (aryloxycarbonylamino group with 7 to 12 carbon atoms, preferably 7 to 9 carbon atoms, for example, phenoxycarbonylamino, p-chlorophenoxycarbonylamino, 4-methoxyphenoxycarbonylamino), sulfamoylamino group (sulfamoylamino group with zero to 10 carbon atoms, preferably zero to 6 carbon atoms, for example sulfamoylamino, N,N-dimethylaminosulfonylamino, N-(2-hydroxyethyl)sulfamoylamino), alkylsulfonylamino group (alkylsulfonylamino group with one to 10 carbon atoms, preferably one to 6 carbon atoms, for example, methylsulfonylamino, butylsulfonylamino), arylsulfonylamino group (arylsulfonylamino group with 6 to 12 carbon atoms, preferably 6 to 8 carbon atoms, for example, phenylsulfonylamino, 2,3,5-trichlorophenylsulfonylamino, p-methylphenylsulfonylamino), mercapto group, alkylthio group (alkylthio group with one to 10 carbon atoms, preferably one to 6 carbon atoms, for example methylthio, ethylthio, butylthio), arylthio group (arylthio with 6 to 12 carbon atoms, preferably 6 to 8 carbon atoms, for example, phenylthio, p-chlorophenylthio, m-methoxyphenylthio), hetero-ring thio group (hetero-ring thio group with 2 to 10 carbon atoms, preferably one to 6 carbon atoms, for example 2-benzothiazolylthio, 1-phenyltetrazol-5-ylthio), sulfamoyl group (sulfamoyl group with zero to 10 carbon atoms, preferably zero to 6 carbon atoms, for example, sulfamoyl, N-ethylsulfamoyl, N,N-dimethylsulfamoyl, N-acetylsulfamoyl, N-benzoylsulfamoyl), alkylsulfinyl group (alkylsulfinyl group with one to 10 carbon atoms, preferably one to 6 carbon atoms, for example, methylsulfinyl, ethylsulfinyl), arylsulfinyl group (arylsulfinyl group with 6 to 12 carbon atoms, preferably 6 to 8 carbon atoms, for example, phenylsulfinyl, p-methylphenylsulfinyl), alkylsulfonyl group (alkylsulfonyl group with one to 10 carbon atoms, preferably one to 6 carbon atoms, for example, methylsulfonyl, ethylsulfonyl), arylsulfonyl group (arylsulfonyl group with 6 to 12 carbon atoms, preferably 6 to 8 carbon atoms, for example, phenylsulfonyl, p-chlorophenylsulfonyl), acyl group (formyl group, alkylcarbonyl group with 2 to 10 carbon atoms, preferably 2 to 6 carbon atoms, or arylcarbonyl group with 7 to 12 carbon atoms, preferably 7 to 9 carbon atoms, including for example acetyl, pivaloyl, 2-chloroacetyl, benzoyl, 2,4-dichlorobenzoyl), alkoxycarbonyl group (alkoxycarbonyl group with 2 to 10 carbon atoms, preferably 2 to 6 carbon atoms, for example, methoxycarbonyl, ethoxycarbonyl, t-butoxycarbonyl, isobutyloxycarbonyl), aryloxycarbonyl group (aryloxycarbonyl group with 7 to 12 carbon atoms, preferably 7 to 9 carbon atoms, for example, phenoxycarbonyl, 2-chlorophenoxycarbonyl, 3-nitrophenoxycarbonyl, 4-t-butylphenoxycarbonyl), carbamoyl group (carbamoyl group with one to 10 carbon atoms, preferably one to 6 carbon atoms, for example, carbamoyl, N-methylcarbamoyl, N,N-dimethylcarbamoyl, N-(2-hydroxyethyl)carbamoyl, N-(methylsulfonyl)carbamoyl), arylazo group (arylazo group with 6 to 12 carbon atoms, preferably 6 to 8 carbon atoms, for example phenylazo, p-chlorophenylazo), hetero-ring azo group (hetero-ring azo group with one to 10 carbon atoms, preferably one to 6 carbon atoms, for example, pyrazol-3-ylazo, thiazol-2-ylazo, 5-ethylthio-1,3,4-thiadiazol-2-ylazo), imido group (imido group with 2 to 10 carbon atoms, preferably 4 to 8 carbon atoms, for example, N-succinimido, N-phthalimido), phosphino group (phosphino group with 2 to 12 carbon atoms, preferably 2 to 6 carbon atoms, for example, dimethylphosphino, diphenylphosphino, methylphenoxyphosphino), phosphinyl group (phosphinyl group with 2 to 12 carbon atoms, preferably 2 to 6 carbon atoms, for example phosphinyl, diethoxyphosphinyl), phosphinyloxy group (phosphinyloxy group with 2 to 12 carbon atoms, preferably 2 to 6 carbon atoms, for example, diphenoxyphosphinyloxy, dibutoxyphosphinyloxy), phosphinylamino group (phosphinylamino group with 2 to 12 carbon atoms, preferably 2 to 6 carbon atoms, for example, dimethoxyphosphinylamino, dimethylaminophosphinylamino), and silyl group (silyl group with 3 to 12 carbon atoms, preferably 3 to 8 carbon atoms, for example, trimethylsilyl, t-butyldimethylsilyl, phenyldimethylsilyl). These groups may further contain substituents, and preferably, such substituents then include the groups with the same meaning as described as the preferable substituent for the phenyl or naphthyl group represented by "A". In the case that these groups are substituted with 2 or more substituents, the substituents may be the same or different.

Particularly preferably, the substituent for the phenyl or naphthyl group represented by "A" is a halogen atom, alkyl group, aryl group, hetero-ring group, cyano group, hydroxy group, nitro group, alkoxy group, aryloxy group, amino group (including anilino group), acylamino group, aminocarbonylamino group, alkoxycarbonylamino group, alkylsulfonylamino group, arylsulfonylamino group, alkylthio group, arylthio group, hetero-ring thio group, sulfamoyl group, alkylsulfonyl group, arylsulfonyl group, acyl group, alkoxycarbonyl group, and carbamoyl group; more preferably, the substituent is halogen atom, alkyl group, cyano group, hydroxy group, nitro group, alkoxy group, amino group (including anilino group), acylamino group, alkylsulfonylamino group, carbamoyl group, sulfamoyl group, alkylsulfonyl group and arylsulfonyl group.

Above all, the substituent is preferably an electron withdrawing group having a Hammet's constant value $\sigma_p$ of not less than about 0.1, such as a halogen atom, cyano group, nitro group, sulfamoyl group, alkylsulfonyl group and arylsulfonyl group. Hammet's rule is an empirical rule suggested by L. P. Hammet in 1935 in order to quantitatively discuss the effects of a substituent of a benzene derivative on the reaction or equilibrium thereof, which rule has been widely acknowledged. According to Hammet's rule, there are two kinds of values, $\sigma_p$ and $\sigma_m$ values, as a coefficient of substitution. These values are described in many books, for instance, J. A. Dean "Lange's Handbook of Chemistry", 12th edition, 1979 (McGraw-Hill); "Kagakunoryouiki-zoukan" 122, 96–103, 1979 (Nankodo); and "Chemical Review", 91, 165–195, 1991.

Throughout the specification, any reference to a hetero-ring compound means a compound comprising a heteroatom containing group containing at least one heteroatom selected from the group consisting of N, O and S. "B" in the azo dye represented by general formula (1) represents an atomic group essential for the formation of a dissociative azo dye from the compound represented by general formula (1) and is preferably derived from a coupler component. Herein, the coupler component means a partial structure derived from a coupler compound capable of reacting with a diazonium salt to give an azo dye. The concept is commonly used in the field of azo dyes. "B" in the azo dye represented by general formula (1) has preferably 3 to 30 carbon atoms, more preferably 3 to 20 carbon atoms, most preferably 3 to 12 carbon atoms, inclusive of the substituents therein.

The coupler component is preferably a coupler component known in the field of silver halide colour photographic materials, and as such, use can be made of the backbone moiety of a colour coupler (the moiety serving as a dye chromophore via coupling with an aromatic amine-based developing agent, such as p-phenylenediamine), which is described in detail for example in Research Disclosure 37038 (February 1995), pages 80–85, and 87–89.

The coupler known as a coupler forming yellow-colored image in the field of silver halide colour photographic materials includes for example couplers of the pivaloylacetamide type, benzoylacetamide type, malondiester type, malondiamide type, dibenzoylmethane type, benzothiazolylacetamide type, malonestermonoamide type, benzoxazolylacetamide type, benzoimidazolylacetamide type, cyanoacetamide type, cycloalkylcarbonylacetamide type, indolin-2-ylacetamide type, quinazolin-4-on-2-ylacetamide type described in U.S. Pat. No. 5,021,332, the benzo-1,2,4-thiadiazine-1,1-dioxid-3-ylacetamide type described in U.S. Pat. No. 5,021,330, the coupler described in EP 421221A, the coupler described in U.S. Pat. No. 5,455,149, the coupler described in EP 0622673A, the couplers of 3-indoloylacetamide type described in EP 0953871A, 0953872A and 0953873A, as preferable coupler backbones.

The coupler known as a coupler forming magenta-colored images in the field of silver halide colour photographic materials includes for example couplers of 5-pyrazolone type, 1H-pyrazolo[1,5-a]benzimidazole type, 1H-pyrazolo[5,1-c][1,2,4]triazole type, 1H-pyrazolo[1,5-b][1,2,4]triazole type, 1H-imidazo[1,2-b]pyrazole type, cyanoacetophenone type, the active propene type described in WO 93/01523, and the enamine type described in WO 93/07534, the 1H-imidazo[1,2-b][1,2,4]triazole type coupler and the coupler described in U.S. Pat. No. 4,871,652, as preferable coupler backbones.

The coupler known as a coupler forming cyan-colored images in the field of silver halide colour photographic materials includes for example couplers of the phenol type, naphthol type, the 2,5-diphenylimidazole type, 1H-pyrrolo[1,2-b][1,2,4]triazole type, and 1H-pyrrolo[2,1-c][1,2,4]triazole type as described in EP 0249453A, the pyrrole type described in Japanese Patent Application Laid-open Nos. 188137/1992 and 190347/1992, 3-hydroxypyridine type described in Japanese Patent Application Laid-open No. 315736/1989, pyrrolopyrazole type described in U.S. Pat. No. 5,164,289, the pyrroloimidazole type described in Japanese Patent Application Laid-open No. 174429/1992, and the pyrazolopyrimidine type described in U.S. Pat. No. 4,950,585, and the pyrrolotriazine type coupler described in Japanese Patent Laid-open No. 204730/1992, the coupler described in U.S. Pat. No. 4,746,602, the coupler described in U.S. Pat. No. 5,104,783, the coupler described in U.S. Pat. No. 5,162,196, and the coupler described in EP 0556700, as preferable coupler backbones.

The group represented by "B" in the azo dye represented by general formula (1) preferably includes groups represented by the following structures (B-1) to (B-12).

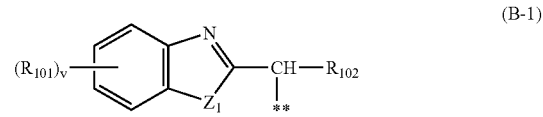
(B-1)

(B-2)

(B-3)

(B-4)

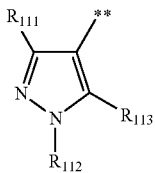
(B-5)

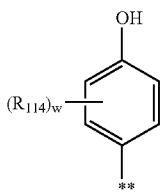
(B-6)

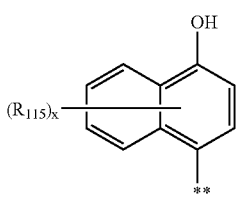
(B-7)

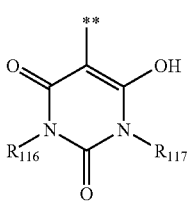
(B-8)

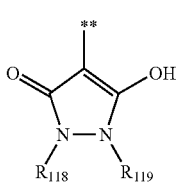
(B-9)

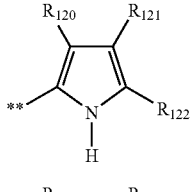
(B-10)

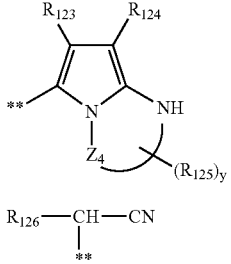
(B-11)

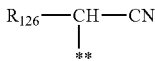
(B-12)

In the formulas, the symbol "**" expresses the position where the groups bind to the azo group in general formula (1).

In formula (B-1), $R_{101}$ represents a halogen atom, alkyl group, aryl group, hetero-ring group, cyano group, alkoxy group, amino group (including anilino group), acylamino group, alkylsulfonylamino group, arylsulfonylamino group, alkylthio group, arylthio group, sulfamoyl group, alkylsulfonyl group, or carbamoyl group. $R_{102}$ represents a cyano group, alkylsulfonyl group, arylsulfonyl group, acyl group, alkoxycarbonyl group, aryloxycarbonyl group, or carbamoyl group. $Z_1$ represents an oxygen atom, sulfur atom, or —N($R_{103}$)—. $R_{103}$ represents hydrogen atom, alkyl group, aryl group or hetero-ring group. "v" represents an integer of from 0 to 4. Provided that v is a plural number, the $R_{101}$ groups in the number "v" may be the same or different. $R_{101}$ is preferably a halogen atom, acylamino group, alkylsulfonylamino group, sulfamoyl group, and carbamoyl group. $R_{102}$ is preferably a cyano group, and carbamoyl group. $Z_1$ is preferably an oxygen atom, sulfur atom, or —N($R_{103}$)— where $R_{103}$ is an alkyl group.

In formula (B-2), $R_{104}$ represents a cyano group, alkylsulfonyl group, arylsulfonyl group, acyl group, alkoxycarbonyl group, aryloxycarbonyl group, or carbamoyl group; $R_{105}$ and $R_{106}$ independently represent a hydrogen atom, alkyl group, aryl group, or hetero-ring group. Preferably, $R_{104}$ is a cyano group, acyl group, and carbamoyl group, while one of $R_{105}$ and $R_{106}$ is preferably a hydrogen atom.

In formula (B-3), $R_{107}$ represents a hydrogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, or carbamoyl group; $Z_2$ and $Z_3$ independently represent —C($R_{108}$)= or —N=; $R_{108}$ represents an alkyl group, aryl group, hetero-ring group, alkylthio group, arylthio group, alkoxycarbonyl group, or carbamoyl group. Provided that $Z_2$ and $Z_3$ both represent —C($R_{108}$)=, two $R_{108}$ groups may be the same or different or may bind together to form a carbon ring or a hetero-ring. $R_{107}$ is preferably a hydrogen atom, alkyl group and aryl group, more preferably a hydrogen atom and alkyl group, and $R_{108}$ is preferably an alkyl group, aryl group, and hetero-ring group, more preferably alkyl group.

In the formula (B-4), $R_{109}$ represents an alkyl group, aryl group or hetero-ring group, and $R_{110}$ represents a hydrogen atom, alkyl group, aryl group, hetero-ring group, acyl group, alkylsulfonyl group or arylsulfonyl group. $R_{109}$ is preferably an alkyl group and aryl group, and $R_{110}$ is preferably a hydrogen atom and alkyl group.

In formula (B-5), $R_{111}$ represents a hydrogen atom, alkyl group, aryl group, alkoxy group, amino group (including anilino group), alkoxycarbonyl group, cyano group, acylamino group, or carbamoyl group; $R_{112}$ represents a hydrogen atom, alkyl group, aryl group, or hetero-ring group; $R_{113}$ represents a hydroxy group or amino group. $R_{111}$ is preferably an alkoxycarbonyl group, cyano group, and carbamoyl group; $R_{112}$ is preferably an alkyl group and aryl group.

In formula (B-6), $R_{114}$ represents a halogen atom, alkyl group, aryl group, hetero-ring group, nitro group, alkoxy group, aryloxy group, amino group (including anilino group), acylamino group, alkoxycarbonylamino group, aminocarbonylamino group, alkylsulfonylamino group, arylsulfonylamino group, alkylthio group, arylthio group, hetero-ring thio group, alkoxycarbonyl group, or carbamoyl group; "w" represents an integer of from 0 to 4. Provided that "w" is a plural number, the $R_{114}$ groups in the number "w" may be the same or different. $R_{114}$ is preferably a halogen atom, alkyl group, acylamino group, alkoxycarbonylamino group, aminocarbonylamino group, alkylsulfonylamino group, arylsulfonylamino group, and carbamoyl group, more preferably a halogen atom, alkyl group, acylamino group, and alkylsulfonylamino group.

In formula (B-7), $R_{115}$ represents a halogen atom, alkyl group, aryl group, hetero-ring group, nitro group, alkoxy group, aryloxy group, amino group (including anilino group), acylamino group, alkoxycarbonylamino group, aminocarbonylamino group, alkylsulfonylamino group, arylsulfonylamino group, alkylthio group, arylthio group, heteroring thio group, alkoxycarbonyl group or carbamoyl group; "x" represents an integer of 0 to 6. Provided that "x" is a plural number, the $R_{115}$ groups in the number "x" may be the same or different. $R_{115}$ is preferably a halogen atom, acylamino group, alkoxycarbonylamino group, aminocarbonylamino group, arylsulfonylamino group, and carbamoyl group, more preferably an acylamino group, alkylsulfonylamino group, and carbamoyl group.

In formula (B-8), $R_{116}$ and $R_{117}$ independently represent an alkyl group or aryl group, and these groups are preferably the same.

In formula (B-9), $R_{118}$ and $R_{119}$ independently represent an alkyl group or aryl group, and these groups are preferably the same.

In formula (B-10), $R_{120}$ and $R_{121}$ independently represent an alkyl group, aryl group, hetero-ring group, cyano group, alkylsulfonyl group, arylsulfonyl group, alkoxycarbonyl group, or carbamoyl group; $R_{122}$ represents a hydrogen atom, alkyl group, aryl group, hetero-ring group, acylamino group, alkylsulfonylamino group, or arylsulfonylamino group. Preferably, $R_{120}$ and $R_{121}$ are an alkyl group, aryl group, hetero-ring group, or cyano group. Preferably, $R_{122}$ is a hydrogen atom, alkyl group, aryl group, acylamino group, and alkylsulfonylamino group.

In formula (B-11), $R_{123}$ and $R_{124}$ independently represent an alkyl group, aryl group, hetero-ring group, cyano group, alkylsulfonyl group, arylsulfonyl group, alkoxycarbonyl group, or carbamoyl group; $Z_4$ represents a non-metal atomic group forming a 5-membered or 6-membered ring, together with the two nitrogen atoms and the one carbon atom to which it is attached. $R_{125}$ represents an alkyl group, aryl group, alkoxy group, amino group, acylamino group, alkylsulfonylamino group, arylsulfonylamino group, alkylthio group, arylthio group, acyl group, alkoxycarbonyl group, or carbamoyl group; "y" represents an integer of from 0 to 2, provided that $Z_4$ forms a 5-membered ring; and "y" represents an integer of from 0 to 3, provided that $Z_4$ forms a 6-membered ring. Preferably, $R_{123}$ is an alkyl group, aryl group, hetero-ring group, or cyano group. Preferably, $R_{124}$ is an alkylsulfonyl group, arylsulfonyl group, alkoxycarbonyl group, and carbamoyl group. $R_{125}$ is preferably an alkyl group, aryl group, alkylthio group, amino group, and acylamino group.

In formula (B-12), $R_{126}$ represents an alkyl, aryl group, cyano group or alkoxy carbonyl group.

In formulas (B-1) to (B-12), the preferred number of carbon atoms and specific examples of the individual groups listed in the descriptions of the groups represented by $R_{101}$ to $R_{126}$ are the same as those listed in the description of the substituent for the phenyl or naphthyl group represented by A. Also the heteroatom containing groups have the same meaning as outlined above.

In case that $R_{101}$ to $R_{126}$ in formulas (B-1) to (B-12) are groups with a possibility of additional substitution, $R_{101}$ to $R_{126}$ may further have a substituent, and the substituent in that case is the same as the substituent listed for the phenyl or naphthyl group represented by "A".

Dyes represented by the following formulas DS-1 to DS-9 among compounds represented by general formula (1) are particularly preferable. "A" in the general formulas DS-1 to DS-9 represents a group with the same meaning as that of "A" in the general formula (1).

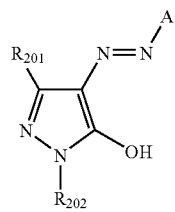

DS-1

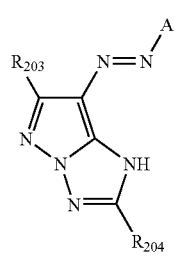

DS-2

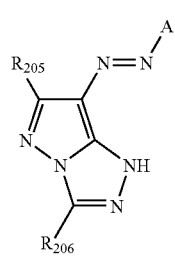

DS-3

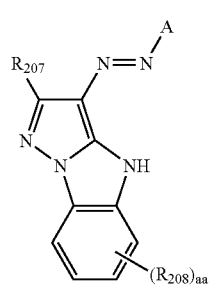

DS-4

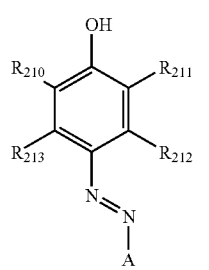

DS-5

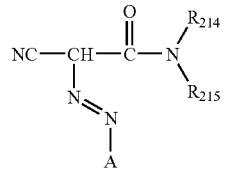

DS-6

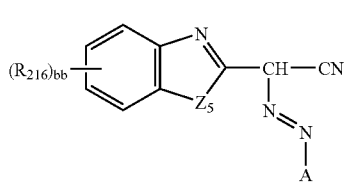

DS-7

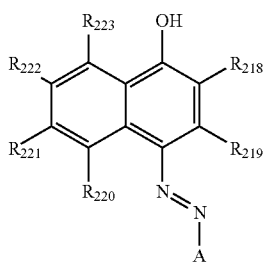

DS-8

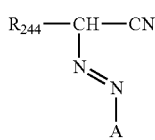

DS-9

In formula DS-1, $R_{201}$ represents a hydrogen atom, alkyl group, aryl group, alkoxy group, amino group (including anilino group), alkoxycarbonyl group, cyano group, acylamino group, or carbamoyl group; $R_{202}$ represents a hydrogen atom, alkyl group, aryl group, or hetero-ring group. Preferably, $R_{201}$ is an alkoxycarbonyl group, cyano group, and carbamoyl group and $R_{202}$ is an alkyl group and aryl group.

In formula DS-2, $R_{203}$ represents a hydrogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, or carbamoyl group; $R_{204}$ represents an alkyl group, aryl group, or hetero-ring group. $R_{203}$ is preferably a hydrogen atom and alkyl group, and the alkyl group particularly preferably includes a methyl group, ethyl group, isopropyl group, and t-butyl group. $R_{204}$ is most preferably an alkyl group.

In formula DS-3, $R_{205}$ represents a hydrogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, or carbamoyl group; $R_{206}$ represents an alkyl group, aryl group, hetero-ring group, alkylthio group, arylthio group, alkoxycarbonyl group, or carbamoyl group. $R_{205}$ is preferably a hydrogen atom and alkyl group, and the alkyl group particularly preferably includes a methyl group, ethyl group, isopropyl group, and t-butyl group. $R_{206}$ is preferably an alkyl group, aryl group, or alkylthio group, most preferably an alkyl group.

In formula DS-4, $R_{207}$ represents a hydrogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, or carbamoyl group; $R_{208}$ represents a halogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, alkoxycarbonyl group, or carbamoyl group; "aa " represents an integer of from 0 to 4; provided that when "aa" is 2 to 4, the $R_{208}$ groups may be same or different. Preferably, $R_{207}$ is a hydrogen atom and alkyl group, and the alkyl group particularly preferably includes a methyl group, ethyl group, isopropyl group, and t-butyl group. $R_{208}$ is preferably a halogen atom, alkyl group, alkoxy group, acylamino group, and alkylsulfonylamino group.

In formula DS-5, $R_{210}$ and $R_{211}$ independently represent a hydrogen atom, halogen atom, alkyl group, aryl group, acylamino group, alkoxycarbonyl group, aminocarbonylamino group, alkylsulfonylamino group, arylsulfonylamino group, alkoxycarbonylamino group, or carbamoyl group; $R_{212}$ and $R_{213}$ independently represent a hydrogen atom, halogen atom, alkyl group, alkoxy group, or acylamino group. $R_{210}$ and $R_{211}$ preferably represent a hydrogen atom, chlorine atom, bromine atom, alkyl group, and acylamino group. $R_{212}$ and $R_{213}$ preferably independently represent a hydrogen atom, chlorine atom, bromine atom, alkyl group, and acylamino group. More specifically, at least one of $R_{212}$ and $R_{213}$ is a hydrogen atom.

In formula DS-6, $R_{214}$ and $R_{215}$ independently represent a hydrogen atom, alkyl group, aryl group, or hetero-ring group, and one of $R_{214}$ and $R_{215}$ is preferably hydrogen atom.

In formula DS-7, $R_{216}$ represents a halogen atom, alkyl group, aryl group, hetero-ring group, cyano group, alkoxy group, amino group (including anilino group), acylamino group, alkylsulfonylamino group, arylsulfonylamino group, alkylthio group, arylthio group, sulfamoyl group, alkylsulfonyl group, or carbamoyl group; $Z_5$ represents an oxygen atom, sulfur atom, or —N($R_{217}$)—, where $R_{217}$ represents a hydrogen atom, alkyl group, aryl group, or hetero-ring group. "bb" represents an integer of from 0 to 4. Provided that "bb" is a plural number, the $R_{216}$ groups in the number "bb" may be the same or different. $R_{216}$ is preferably a halogen atom, acylamino group, alkylsulfonylamino group, sulfamoyl group, and carbamoyl group. Preferably, $Z_5$ is an oxygen atom, sulfur atom, and —N($R_{217}$)—, where $R_{217}$ is an alkyl group. More preferably, $Z_5$ is an oxygen atom and sulfur atom.

In formula DS-8, $R_{218}$ represents a hydrogen atom, halogen atom, alkyl group, aryl group, acylamino group, alkylsulfonylamino group, arylsulfonylamino group, alkoxycarbonylamino group, aminocarbonylamino group, carbamoyl group, or sulfamoyl group; $R_{220}$ and $R_{223}$ independently represent a hydrogen atom, halogen atom, acylamino group, alkoxycarbonylamino group, aminocarbonylamino group, alkylsulfonylamino group, or arylsulfonylamino group; $R_{219}$, $R_{221}$, and $R_{222}$ independently represent a hydrogen atom, chlorine atom, bromine atom, alkyl group, or acylamino group. $R_{218}$ is preferably a hydrogen atom, acylamino group, alkylsulfonylamino group, arylsulfonylamino group, alkoxycarbonylamino group, aminocarbonylamino group, carbamoyl group, and sulfamoyl group. $R_{220}$ and $R_{223}$ are preferably independently a hydrogen atom, acylamino group, alkoxycarbonylamino group, and alkylsulfonylamino group. $R_{219}$, $R_{221}$, and $R_{222}$ are preferably hydrogen atoms.

In formula DS-9, $R_{224}$ represents an alkyl, aryl group cyano group or alkoxycarbonyl group.

In formulas DS-1 to DS-9, preferable carbon numbers and specific examples of the individual groups listed in the descriptions of the groups represented by $R_{201}$ to $R_{224}$ are the same as those listed in the description of the substituent for the phenyl or naphthyl group represented by "A".

Provided that $R_{201}$ to $R_{224}$ in formulas DS-1 to DS-9 are groups with a possibility of additional substitutions, $R_{201}$ to $R_{224}$ may have additional substituents. The substituents then are the same as those listed in the description of the substituent for the hetero-ring group represented by "A".

Specific compound examples of the dissociative azo dyes represented by general formula (1) in accordance with the invention are described below, but the invention is not limited to these examples.

D-1
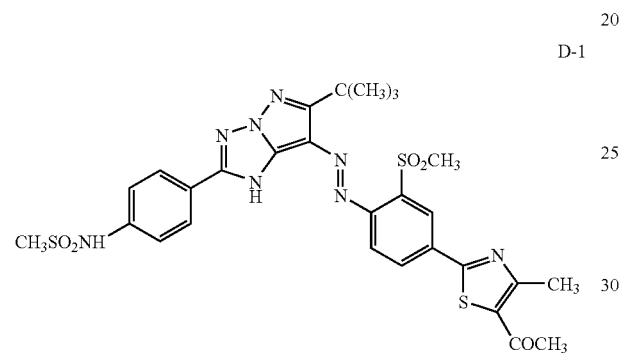

D-2
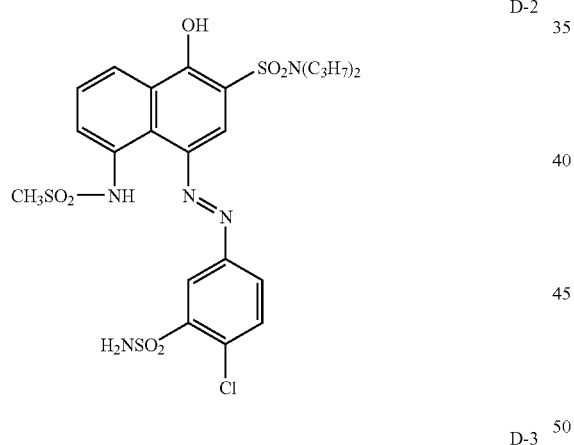

D-3
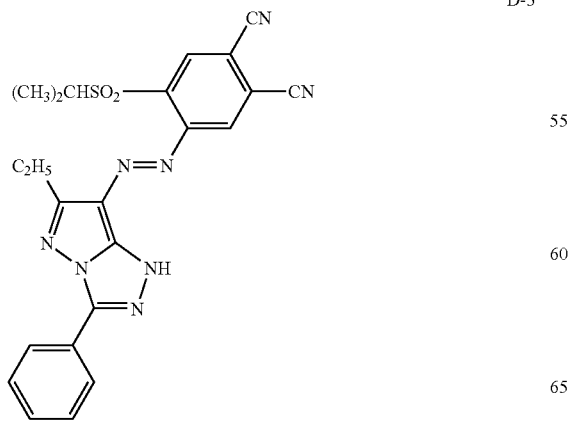

D-4
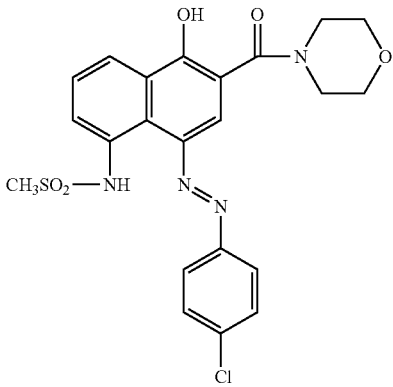

D-5
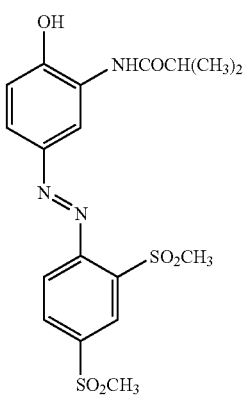

D-6
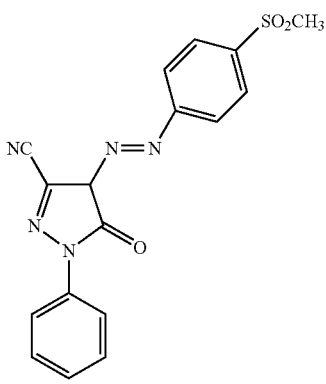

D-7
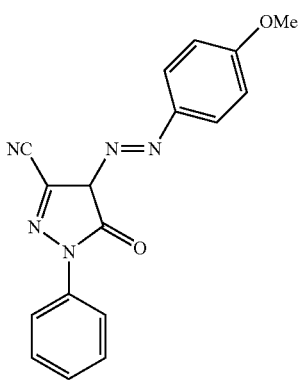

-continued
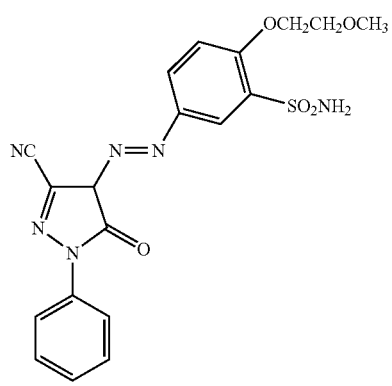 D-8
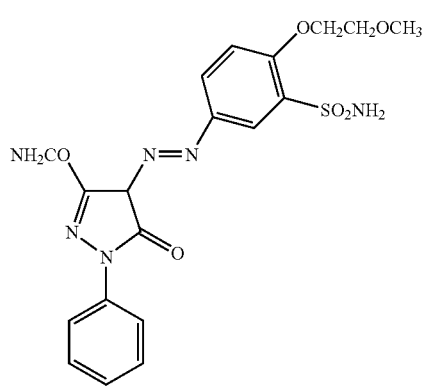 D-9
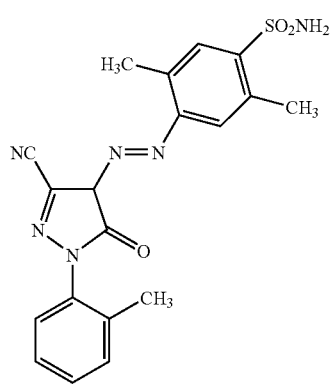 D-10
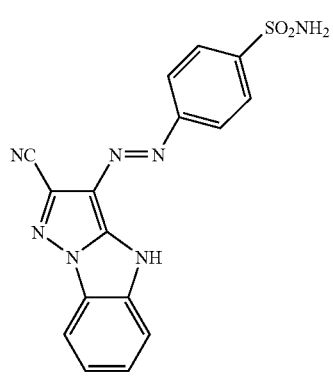 D-11
-continued
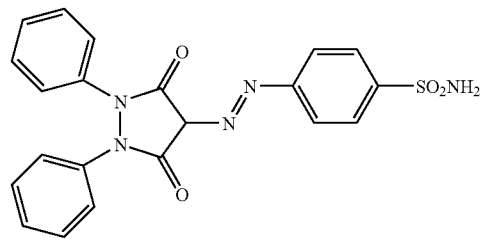 D-12
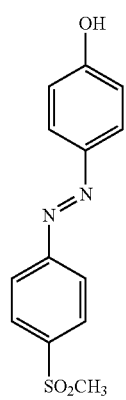 D-13
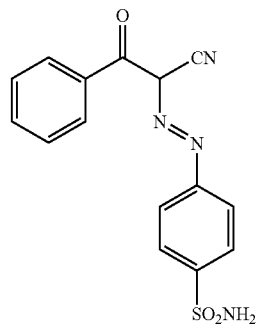 D-14
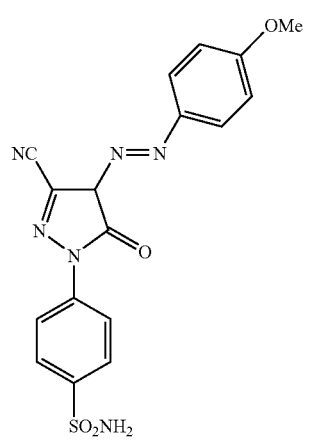 D-15

-continued
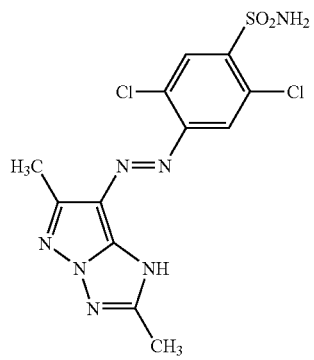
D-16
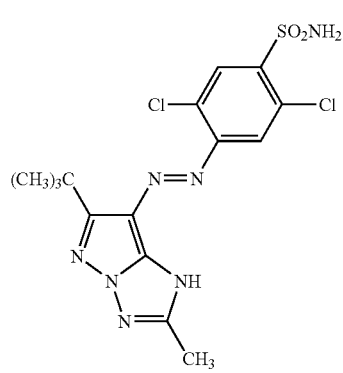
D-17
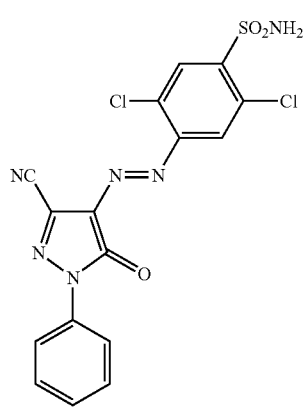
D-18
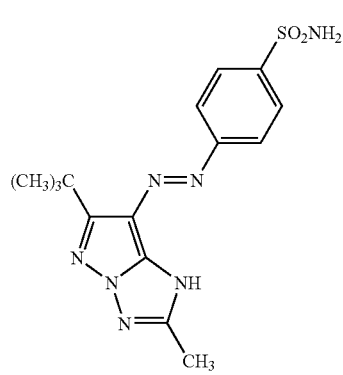
D-19
-continued
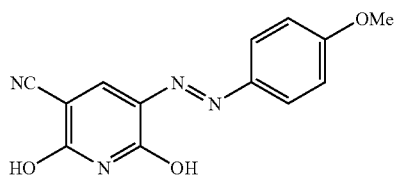
D-20
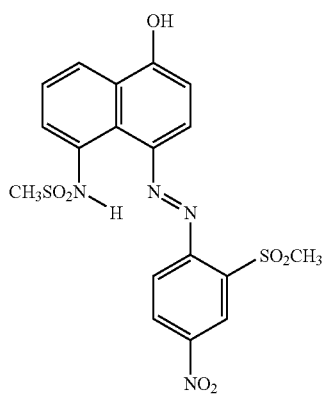
D-21
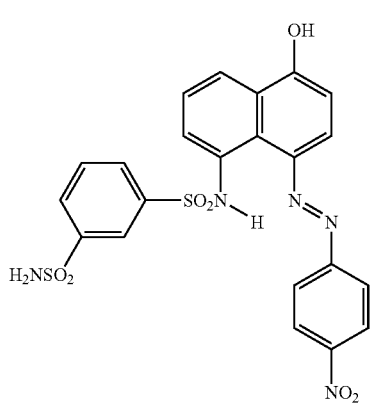
D-22
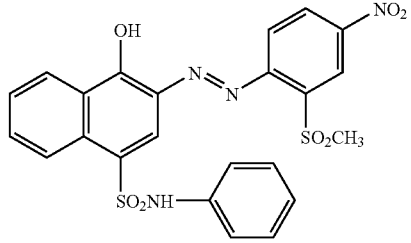
D-23
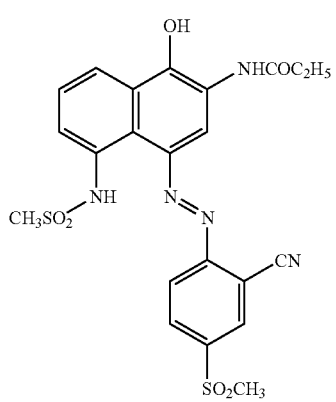
D-24

-continued

D-25
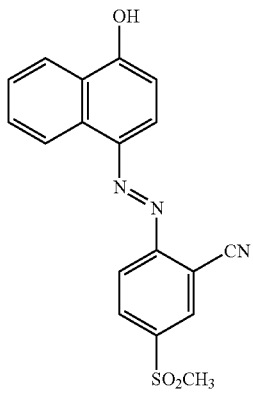

D-26
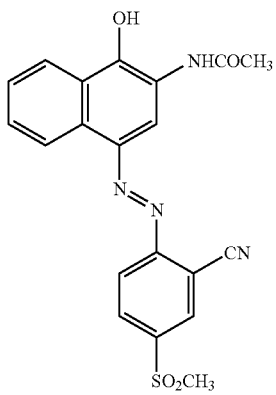

D-27
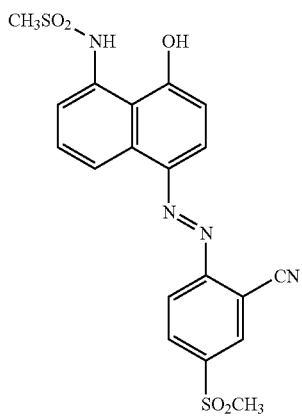

D-28
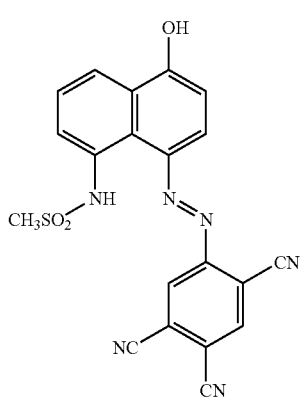

D-29
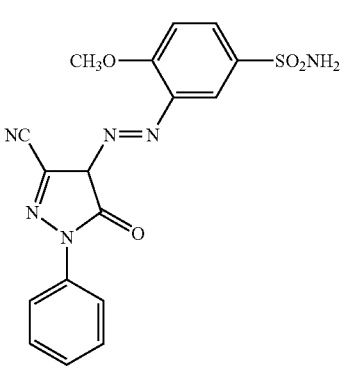

In the preferred embodiments of the present invention, dissociative dyes are to be understood to mean those dyes that contain at least one group having a pKa value preferably falling within the range of from about 1.5 to 9, more preferably from about 2 to 8 and even more preferably from about 2 to 7.5. It is most preferred that the dissociative dyes do not contain any groups having a pKa value of below about 1.5. The pKa of the azo dyes is one possibility for determining the dyeing power of the dyes. The groups having a pKa value of from about 1.5 to 9 are for example phenolic OH-groups, CH-acidic groups (active methylene, active methine), —NH-groups in conjugated heterocyclic rings, OH-groups attached to the conjugated heterocyclic rings and the like.

The pKa value is determined in DMF/water (1/1-mixture, by volume) as follows:

The dye is dissolved in a solution of a DMF/water (1/1; volume ratio) to a final concentration of $2 \times 10^{-5}$ mol/l. After the resulting solution is adjusted to pH 2, using 1.0 mol/l hydrochloric acid, the solution is titrated with an aqueous 1.0 mol/l sodium hydroxide solution. Recording the change of the visible ultra-violet absorption spectrum, the inflection point is determined by regression analysis.

The dissociative azo dye represented by formula (1) has a dissociative proton in the chromophore of the dye. The hue of the dye in an aqueous medium may change at a higher pH due to the dissociation of the proton and the formation of the anionic dye.

In another aspect of the present invention, there is also provided a hair dyeing method comprising applying the above-described hair dye composition to the hair.

One or more of the above mentioned, particularly preferred azo direct dyes D-1 to D-29 can be used. Additionally, it may be used in combination with another direct dye or with oxidative dyes.

Examples of additional direct dyes that can be used in combination with the direct dyes of the invention include, Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 12 (C.I. 48070), Basic Red 22 (C.I. 11055), Basic Red 46 (C.I. 110825), Basic Red 76 (C.I. 12245), Basic Red 118 (C.I. 12251:1), Basic Yellow 28 (C.I. 48054) and Basic Yellow 57 (C.I. 12719); cationic dyes as described in Japanese Patent Publication No. Sho 58-2204, Japanese Patent Application Laid-Open (kokai) No. Hei 9-118832, Japanese Patent Laid-Open Publications (PCT) Nos. Hei 8-501322 and Hei 8-507545; and methine type cationic dyes having a cyanine structure represented by the below-described formulas:

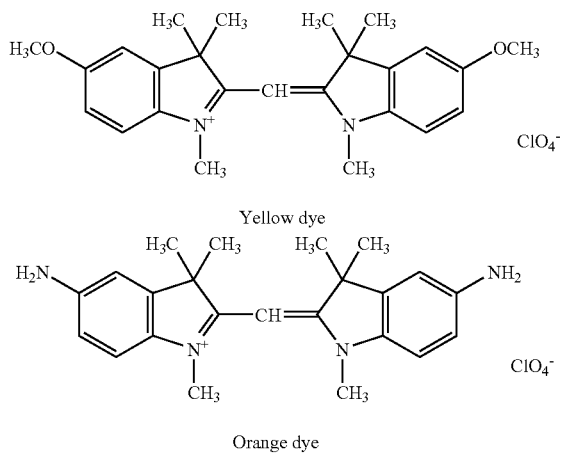

Yellow dye

Orange dye

The azo dyes represented by formula (1) are preferably added in an amount of from about 0.0001 to 20 wt. %, more preferably from about 0.001 to 20 wt. %, even more preferably from about 0.05 to 10 wt. %, even more preferably from about 0.1 to 5 wt. %, based on the whole composition (after mixing of all the component parts; when the composition is a two part or three part composition; this will be applied equally hereinafter). When another dye is used in combination with the direct dye (1), the total amount of dyes is preferably from about 0.001 to 20 wt. %, more preferably from about 0.01 to 20 wt. %, even more preferably in the range from about 0.05 to 10 wt. %, even more preferably from about 0.1 to 5 wt. %, based on the whole composition.

In the preferred hair dye composition of the present invention, the direct dye (1) exhibits high storage stability within a wide pH range from 2 to 11 which is a pH range employed ordinarily for hair dyes, so that the hair dye composition can be used freely in the above-described pH range. Use in a pH range of 5 or greater is however preferred from the viewpoint of dyeing properties. Moreover, owing to high stability of the direct dye against an alkaline agent, the hair dye composition can be used at a pH above 8, particularly from 8 to 11 which permits a high dyeing power, and even after storage for a long period of time, it exhibits high dyeing power without decomposition of the direct dye.

Examples of the alkaline agent that may be used in the dyeing composition include ammonia, alkanolamines such as monoethanolamine and isopropanolamine or salts thereof, guanidium salts such as guanidine carbonate and hydroxide salts such as sodium hydroxide. The alkaline agent is preferably added in an amount of from about 0.01 to 20 wt. %, more preferably from about 0.1 to 10 wt. %, even more preferably from about 0.5 to 5 wt. % based on the whole composition.

Since in the preferred hair dye composition of the present invention, the direct dye (1) has high stability against an oxidizing agent, it can be applied to the hair after mixing with an oxidizing agent. In other words, it can be provided in the form composed of a first component part containing the direct dye (1) and a second component part containing an oxidizing agent. In this case, hair dyeing and bleaching can be carried out simultaneously, which facilitates more vivid hair dyeing. Examples of the oxidizing agent include hydrogen peroxide, persulfates such as ammonium persulfate, potassium persulfate and sodium persulfate, perborates such as sodium perborate, percarbonates such as sodium percarbonate and bromates such as sodium bromate and potassium bromate. Hydrogen peroxide is especially preferred for good hair bleaching properties, stability of the dye and availability. It is also preferred to use a combination of hydrogen peroxide with at least one of the above mentioned other oxidizing agents. The oxidizing agent is preferably added in an amount of from about 0.5 to 10 wt. %, more preferably from about 1 to 8 wt. %, based on the whole composition.

The mixing ratio of the first component part containing the direct dye (1) with the oxidizing-agent-containing second component part preferably ranges from about 2:1 to 1:3 in terms of a volume ratio.

In the preferred hair dye composition of the present invention, the direct dye (1) can also be used in combination with one or more oxidation dyes. The combined use attains a markedly more vivid and stronger colour which is not possible by the use of an oxidation dye alone. For the oxidation dye, known developers and couplers ordinarily employed for an oxidation type hair dye can be used.

Examples of the developer include paraphenylenediamine, toluene-2,5-diamine, 2-chloro-paraphenylenediamine, N-methoxyethyl-paraphenylenediamine, N,N-bis(2-hydroxyethyl)-paraphenylenediamine, 2-(2-hydroxyethyl)-paraphenylenediamine, 2,6-dimethylparaphenylenediamine, 4,4'-diaminodiphenylamine, 1,3-bis(N-(2-hydroxyethyl)-N-(4-aminophenyl)amino)-2-propanol, PEG-3,2,2'-paraphenylenediamine, paraaminophenol, paramethylaminophenol, 3-methyl-4-aminophenol, 2-aminomethyl-4-aminophenol, 2-(2-hydroxyethylaminomethyl)-4-aminophenol, orthoaminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraaminopyrimidine, 2,5,6-triamino-4-hydroxypyrimidine and 4,5-diamino-1-(4'-chlorobenzyl)pyrazole and salts thereof.

Examples of the coupler include metaphenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, metaaminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-metaaminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, and 2,6-diaminopyridine and salts thereof.

At least one of the above-exemplified ones can be used as the developer and coupler. The amount of each of the developer and coupler is preferably from about 0.01 to 20 wt. %, more preferably from about 0.5 to 10 wt. % each based on the whole composition.

To the preferred hair dye composition of the present invention, a known autoxidation dye typified by an indole or an indoline, or a known direct dye such as a nitro dye or a disperse dye can also be added.

The preferred hair dye composition of the present invention may comprise from about 0.01% to about 30% by weight of the composition, preferably from about 0.1% to about 20%, more preferably from about 0.1% to about 10% of a conditioning agent suitable for application to the hair. The conditioning agents are typically polymers or oils which are soluble or dispersible in the hair dye compositions, and are deposited onto the hair when rinsed or diluted with water or shampoo.

Suitable conditioning agents for use in the compositions herein are those conditioning agents characterized generally as silicones (e.g. silicone oils, cationic silicones, silicone gums and silicone resins), organic conditioning oils (e.g. hydrocarbon oils, polyolefins, and fatty esters) or combinations thereof, or those conditioning agents which otherwise form liquid, dispersed particles in the aqueous surfactant.

The conditioning agent of the hair dye compositions of the present invention is preferably an insoluble silicone conditioning agent. The silicone conditioning agent particles may comprise volatile silicone, non-volatile silicone, or combinations thereof. Preferred are non-volatile silicone conditioning agents.

Suitable silicone oils for use herein include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl or polyaryl siloxanes with the following general formula (2):

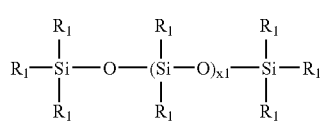

(2)

wherein $R_1$ is aliphatic, preferably alkyl or alkenyl, or aryl, $R_1$ can be substituted or unsubstituted, and x1 is an integer from about 1 to about 8,000.

Non-volatile polyalkylsiloxane fluids that may be used include, for example, low molecular weight polydimethylsiloxanes. These siloxanes are available, for example, from the General Electric Company in their Viscasil R and SF 96 series, and from Dow Corning in their Dow Corning 200 series. Polyalkylaryl siloxane fluids that may be used, also include, for example polymethylphenylsiloxanes. These siloxanes are available, for example, from the General Electric Company as SF 1075 methyl phenyl fluid or from Dow Corning as 556 Cosmetic Grade Fluid. Polyether siloxane copolymers that may be used include, for example, a polypropylene oxide modified polydimethylsiloxane (e.g., Dow Corning DC-1248). Although ethylene oxide or mixtures of ethylene oxide and propylene oxide may also be used, the ethylene oxide and polypropylene oxide concentrations must be sufficiently low to prevent solubility in water and the compositions described herein.

Alkylamino substituted silicones suitable for use herein include, but are not limited to, those of the following general formula (3):

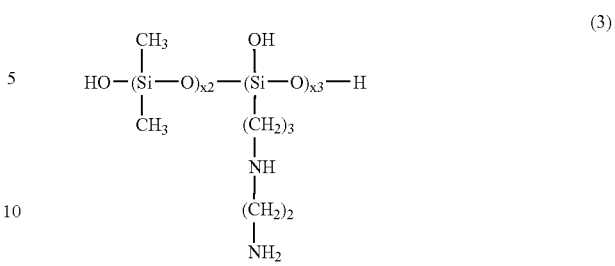

(3)

wherein x2 and x3 are integers. This polymer is also known as "Amodimethicone".

An example of a cationic silicone is the polymer known as "trimethylsilylamodimethicone", which is shown below in formula (4):

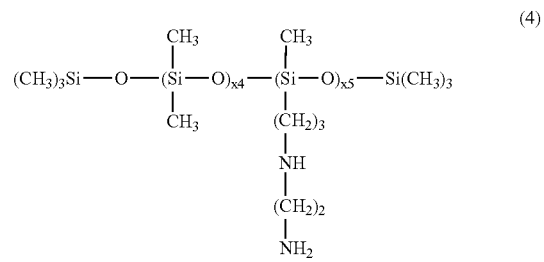

(4)

wherein x4 and x5 are integers.

Other silicone cationic polymers which may be used herein are represented by the general formula (5):

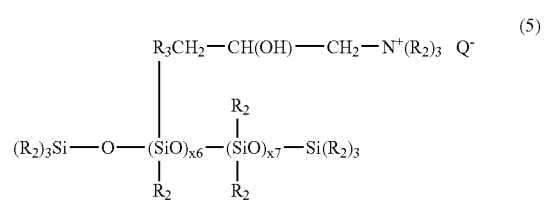

(5)

wherein $R_2$ is a monovalent hydrocarbon radical from $C_1$ to $C_{18}$, preferably an alkyl or alkenyl radical, such as methyl; $R_3$ is a hydrocarbon radical, preferably a $C_1$ to $C_{18}$ alkylene radical or a $C_1$ to $C_{18}$ alkyleneoxy radical, more preferably a $C_1$ to $C_8$ alkyleneoxy radical; $Q^-$ is a halide ion, preferably chloride; x6 is an average statistical value from 2 to 20, preferably from 2 to 8; x7 is an average statistical value from 20 to 200, preferably from 20 to 50.

Other silicone fluids suitable for use herein are the insoluble silicone gums. The silicone gums typically have a weight average molecular weight in excess of about 200,000, preferably from about 200,000 to about 1,000,000. Specific non-limiting examples of silicone gums for use herein include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

Silicone resins may be included in the silicone conditioning agent of the compositions of the present invention. These resins are highly cross-linked polymeric siloxane systems.

The cross-linking is introduced through the incorporation of trifunctional and tetrafunctional silanes with monofunctional or difunctional, or both, silanes during manufacture of the silicone resin.

The conditioning component of the hair dye compositions of the present invention may also comprise from about 0.05% to about 3%, by weight of the composition, preferably from about 0.08% to about 1.5%, more preferably from about 0.1% to about 1%, of at least one organic conditioning oil as the conditioning agent, either alone or in combination with other conditioning agents, such as the silicones as described above. The conditioning oils may add shine and luster to the hair. Additionally, they may enhance dry combing and dry hair feel.

The organic conditioning oils suitable for use as the conditioning agent herein are preferably low viscosity, water insoluble, liquids selected from hydrocarbon oils, polyolefins, fatty esters, and mixtures thereof. The viscosity, as measured at 40° C., of such organic conditioning oils is preferably from about 1 mPa·s to about 200 mPa·s, more preferably from about 1 mPa·s to about 100 mPa·s, even more preferably from about 2 mPa·s to about 50 mPa·s.

Suitable organic conditioning oils for use as conditioning agents in the compositions of the present invention include hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably contain from about 12 to about 19 carbon atoms. Branched chain hydrocarbon oils, including hydrocarbon polymers, typically will contain more than 19 carbon atoms.

Organic conditioning oils for use in the compositions of the present invention can also include liquid polyolefins, more preferably liquid poly-α-olefins, even more preferably hydrogenated liquid poly-α-olefins. Polyolefins for use herein are prepared by polymerisation of $C_4$ to about $C_{14}$ olefinic monomers, preferably from about $C_6$ to about $C_{12}$ olefinic monomers.

Other suitable organic conditioning oils for use as the conditioning agent in the compositions of the present include e.g. fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or other linkages, etc.).

Suitable for use in the compositions of the present invention are alkyl and alkenyl esters of fatty acids having aliphatic chains with from about 10 to 22 carbon atoms, and alkyl and alkenyl fatty alcohol carboxylic acid esters having a $C_{10}$ to about $C_{22}$ alkyl and/or alkenyl alcohol-derived aliphatic chain, and mixtures thereof. Specific examples of preferred fatty esters include isopropyl isostearate, hexyl laurate, isohexyl laurate, isohexyl palmitate, isopropyl palmitate, decyl oleate, isodecyl oleate, hexadecyl stearate, decyl stearate, dihexadecyl adipate, lauryl lactate, myristyl lactate, cetyl lactate, oleyl stearate, oleyl oleate, oleyl myristate, lauryl acetate, cetyl propionate, and dioleyl adipate.

The hair dye compositions of the present invention may contain from about 0.02% to about 5%, by weight of the composition, preferably from about 0.05% to about 3%, more preferably from about 0.1% to about 2%, even more preferably from about 0.5% to about 1%, of at least one organic, cationic deposition and conditioning polymer suitable for application to the hair. Additionally, anionic, non-ionic and/or amphoteric polymers may be incorporated, wherein the total amount of the polymers of any type falls within the above range.

Any anionic counterions may be used in association with the cationic polymers so long as the cationic polymers remain soluble in the composition, and so long as the counterions are physically and chemically compatible with the essential components of the hair dye composition or do not otherwise unduly impair product performance, stability or aesthetics. Non-limiting examples of such counterions include: halide ions (e.g., chloride ion, fluoride ion, bromide ion, iodide ion), sulfate ion, methylsulfate ion, and mixtures thereof. Examples of cationic polymers which may be suitably employed in the hair dye compositions herein include, but are not limited to cationic polysaccharides (e.g. cationic cellulose derivatives and cationic guars), copolymers of vinyl monomers, vinyl pyrrolidone copolymers, cationic modified proteins, and certain polymeric quaternary salts. Such cationic polymers are described in detail below.

Preferred cationic polymers for use in the hair dye compositions of the present invention are those known as cationic polysaccharides. Cationic polysaccharides are those polymers based on $C_5$ to $C_6$ sugars and derivatives which have been made cationic by engrafting of cationic moieties on the polysaccharide backbone, and include homopolymers, copolymers, terpolymers, and so forth, of quaternary ammonium or cationic amine-substituted monomer units, optionally in combination with non-cationic monomers. The polysaccharides may be composed of one type of sugar or of more than one type. The cationic amines can be primary, secondary, or tertiary amines (preferably secondary or tertiary), depending upon the particular species and the selected pH of the hair dye composition. The monomers may be in straight chain or branched chain geometric arrangements. All of the monomer units may have cationic nitrogen-containing moieties attached thereto, preferably some of the monomer units do not have such moieties attached.

Cationic polysaccharide polymers include the following: cationic celluloses, cationic starches and so on.

Suitable polysaccharide cationic polymers for use in the hair dye compositions of the present invention are the cationic cellulose derivatives and cationic starch derivatives. Such cationic polymers include those which conform to general formula (6):

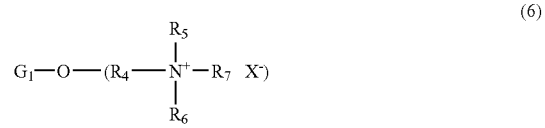

(6)

wherein $G_1$ is an anhydroglucose residual group (e.g. a starch or cellulose anhydroglucose residue); $R_4$ is an alkylene oxyalkylene, polyoxyalkylene, or hydroxyalkylene group, or a combination thereof; $R_5$, $R_6$ and $R_7$ are independently alkyl, aryl, alkylaryl, arylalkyl, alkoxyalkyl, or alkoxyaryl groups, each group containing up to about 18 carbon atoms, and the total number of carbon atoms for each cationic moiety (i.e. the sum of carbon atoms in $R_5$, $R_6$ and $R_7$) preferably being about 20 or less; and $X^-$ is an anionic counterion.

Preferred cationic polymers include, but are not limited to, those polymers available from Amerchol Corporation, in their Polymer JR and LR series of polymers, and salts of hydroxyethyl cellulose reacted with trimethyl ammonium substituted epoxide, known in the industry (CTFA) as Polyquaternium 10 (e.g. JR 30M®, available from Amerchol Corporation). Preferred Polyquaternium 10 polymers for use herein, typically have a charge density from about 0.3 meq/g to about 3 meq/g and a molecular weight from about 200,000 to about 1,500,000. Another non-limiting example of a preferred type of cationic cellulose includes the polymeric quaternary ammonium salt of hydroxyethyl cellulose reacted with lauryl dimethyl ammonium-substituted epoxide, known in the industry (CTFA) as Polyquaternium 24, (e.g. Polymer LM 200®, available from Amerchol Corporation).

Other suitable polysaccharide cationic polymers for use in the hair dye compositions of the present invention are cationic guar polymers. Guars are cationically substituted galactomannan (guar) gum derivatives. The molecular weight of such derivatives ranges typically from about 50,000 to about 2,500,000, preferably from about 50,000 to about 1,000,000, more preferably from about 50,000 to about 700,000.

Guar gum for use in preparing these guar gum derivatives is typically obtained as a naturally occurring material from the seeds of the guar plant. The guar molecule itself is a straight chain mannan branched at regular intervals with single membered galactose units on alternative mannose units. The mannose units are linked to each other by means of β (1–4) glycosidic linkages. The galactose branching arises by way of an α (1–6) linkage. Cationic derivatives of the guar gums are obtained by reaction between the hydroxyl.groups of the polygalactomannan and reactive quaternary ammonium compounds. The degree of substitution of the cationic groups onto the guar structure must be sufficient to provide the preferred cationic charge density described above.

The cationic guar polymer is exemplified by guar hydroxypropyltrimethylammonium chloride, represented by general formula (7), wherein $G_2$ is guar gum:

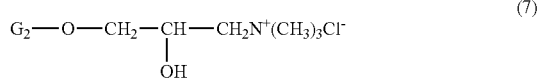

(7)

Other suitable cationic polymers for use in the hair dye compositions of the present invention are copolymers of vinyl monomers, having cationic protonated amine or quaternary ammonium functionalities, reacted with water soluble monomers. Examples of such monomers include: acrylamide, methacrylamide, alkyl and dialkyl acrylamides, alkyl and dialkyl methacrylamides, alkyl acrylate, alkyl methacrylate, vinyl caprolactone, vinyl pyrrolidone, and mixtures thereof. The alkyl and dialkyl substituted monomers preferably have from $C_1$ to $C_7$ alkyl groups, more preferably from $C_1$ to $C_3$ alkyl groups. Other suitable monomers include vinyl esters, vinyl alcohol (made by hydrolysis of polyvinyl acetate), maleic anhydride, propylene glycol, ethylene glycol, and mixtures thereof.

Suitable cationic protonated amino and quaternary ammonium monomers, for inclusion in the cationic polymers of the hair dye composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts; and vinyl quaternary ammonium monomers having cyclic cationic nitrogen-containing rings such as pyridinium, imidazolium, and quaternized pyrrolidones, such as alkyl vinyl imidazolium, alkyl vinyl pyridinium, and alkyl vinyl pyrrolidone salts. The alkyl portions of these monomers are preferably lower alkyl such as the $C_1$–$C_3$ alkyls.

Suitable amine-substituted vinyl monomers for use herein include, dialkylaminoalkyl acrylamide, and dialkylaminoalkyl methacrylamide, wherein the alkyl groups are preferably $C_1$ to $C_7$ hydrocarbyls, more preferably $C_1$ to $C_3$ alkyls.

Other suitable cationic polymers for use in the hair dye compositions of the present invention include: copolymers of 1-vinyl-2-pyrrolidone and 1-vinyl-3-methylimidazolium salt (e.g., chloride salt), known in the industry (CTFA) as Polyquaternium 16 (e.g. Luviquat® FC 370, available from BASF Wyandotte Corporation); copolymers of 1-vinyl-2-pyrrolidone and dimethylaminoethyl methacrylate, known in the industry (CTFA) as Polyquaternium 11 (e.g. Gafquat® 755N, available from ISP Corporation); cationic diallyl quaternary ammonium-containing polymers, including, for example, dimethyldiallyl-ammonium chloride homopolymer, known in the industry (CTFA) as Polyquaternium 6; copolymers of acrylamide and dimethyldiallylammonium chloride, known in the industry (CTFA) as Polyquaternium 7; and mineral acid salts of amino-alkyl esters of homopolymers and copolymers of unsaturated $C_3$ to $C_5$ carboxylic acids.

Still other cationic polymers for use in the hair dye compositions of the present invention are cationic modified proteins, such as lauryldimonium hydroxypropyl collagen (e.g. Croquat® L, available from Croda Corporation) or cocodimonium hydroxypropyl hydrolysed hair keratin (e.g. Croquat® HH, available from Croda Corporation). Other cationic polymers include the polymeric quaternary salt prepared by the reaction of adipic acid and dimethylaminopropylamine, reacted with dichloroethyl ether, known in the industry (CTFA) as Polyquaternium 2 (e.g. Mirapol® AD-1, available from Rhodia), and the polymeric quaternary salt prepared by the reaction of azelaic acid and dimethylaminopropylether, known in the industry (CTFA) as Polyquaternium 18 (e.g. Mirapol® AZ-1, available from Rhodia Corporation).

The hair dye compositions of the present invention may further comprise from about 0.005% to about 1.5% by weight of the composition, preferably from about 0.025% to about 1.2%, more preferably from about 0.05% to about 1%, more preferably from about 0.1% to about 0.5% of selected polyalkylene glycols suitable for application to the hair. Such poylalkylene glycols should be physically and chemically compatible with the essential components described herein, and should not otherwise unduly impair product stability, aesthetics, or performances.

The polyalkylene glycols suitable for use in the hair dye compositions herein are characterized by general formula (8):

(8)

wherein $R_8$ is hydrogen, methyl, or mixtures thereof, preferably hydrogen, and n is an integer having an average value from about 1,500 to about 120,000, preferably from about 1,500 to about 50,000, more preferably from about 2,500 to about 25,000, and even more preferably from about 3,500 to about 15,000. When $R_8$ is hydrogen, these materials are polymers of ethylene oxide, which are also known as polyethylene glycols. When $R_8$ is methyl, these materials are polymers of propylene oxide, which are also known as polypropylene glycols. When $R_8$ is methyl, it is also understood that various positional isomers of the resulting polymers can exist. Preferred for use herein are polyethylene glycols, poylpropylene glycols, and mixtures thereof. Specific non-limiting examples of polyethylene glycol polymers for use in the stable alkaline hair dye compositions of the present invention include: PEG 2M, wherein $R_8$ is hydrogen and n has an average value of about 2,000 (e.g. Polyvox WSR® N-10, available from Union Carbide); PEG 5M, wherein $R_8$ is hydrogen and n has an average value of about 5,000 (e.g. Polyvox WSR® N-35 and Polyvox WSR® N-80, both available from Union Carbide); PEG 7M, wherein $R_8$ is hydrogen and n has an average value of about 7,000 (e.g. Polyvox WSR® N-750, available from Union Carbide); PEG 9M, wherein $R_8$ is hydrogen and n has an average value of about 9,000 (e.g. Polyvox WSR® N-3333, available from Union Carbide); PEG 14 M, wherein $R_8$ is hydrogen and n has an average value of about 14,000 (e.g. Polyvox WSR® N-3000, available from Union Carbide); PEG 23M, wherein $R_8$ is hydrogen and n has an average value of about 23,000 (e.g. Polyvox WSR® N-12k, available from Union Carbide); PEG 90M, wherein $R_8$ is hydrogen and n has an average value of about 90,000 (e.g. Polyvox WSR® 301, available from Union Carbide); and PEG 100M, wherein R is hydrogen and n has an average value of about 100,000 (e.g. Carbowax PEG 4600®, available from Union Carbide). Preferred polyethylene glycols include PEG 7M, PEG 14M, PEG 25M, PEG 90M, and mixtures thereof.

The hair dye compositions of the invention may contain as a further optional component a chelating agent. Chelating agents are understood to act to sequester (chelate or scavenge) heavy metal ions. These components may also have calcium and magnesium chelation capacity, but preferably they show selectivity to binding heavy metal ions such as iron, manganese and copper. Such chelating agents are valuable in hair dye compositions as herein described for the delivery of controlled oxidising action as well as for the provision of good storage stability of the hair coloring products.

Chelating agents are generally present at a level of from about 0.005% to about 20%, preferably from about 0.01% to about 10%, more preferably from about 0.05% to about 2% by weight of the composition.

Various chelating agents, including the amino phosphonates, available as Dequest® from Monsanto, the nitriloacetates, the hydroxyethyl-ethylene triamines and the like are known for such use.

Preferred among the above species are diethylene triamine penta (methylene phosphonate), ethylene diamine tri(methylene phosphonate), hexamethylene diamine tetra (methylene phosphonate) and hydroxy-ethylene-1,1 diphosphonate.

The heavy metal ions sequestering agents may be used in the form of their alkali or alkaline earth metal salts.

The hair dye composition of the present invention can also contain surface-active substances. An anionic, non-ionic, cationic, amphoteric or zwitter-ionic surfactant can be incorporated in the hair dye composition of the present invention, and the above described surfactants are compatible if used together.

Examples of anionic surfactants include sulfate-, sulfonate-, carboxylate- and alkyl phosphate-type surfactants, which are usually used in shampoos.

For example, the well known $C_{10-18}$ alkyl sulfates and in particular the appropriate ether sulfates, for example $C_{12-14}$ alkylether sulfate, laurylether sulfate, in particular with 1 to 4 ethyleneoxide groups in the molecule can be listed as the sulfate-type anionic surfactant. Furthermore, monoglyceride (ether)sulfate, fatty acid amide sulfates which are produced by ethoxylation and following sulfate introduction to the corresponding fatty acid alkanolamide, and their alkali salts as well as salts of long-chained mono and dialkyl phosphates, which represent mild detergent and which can be applied on the hair, also can be used.

Examples of suitable anionic surfactants include alpha-olefinsulfonate or its salts and, in particular, alkali salts of sulfosuccinic acid half-ester, for example disodium salts of the monooctylsulfo succinate and alkali salts of long-chained monoalkylethoxysulfo succinate.

Examples of the suitable carboxylate type surfactants include alkylpolyethercarboxylic acid or their salts and alkamidopolyethercarboxylic acid or their salts.

Such products are well known and have been on the market for a long time, for example under the trade name "AKYPO®" and "AKYPO-SOFT®".

Also $C_{8-20}$ acyl isethionate and likewise sulfofatty acid and their esters can be used, however, in the mixture with other surfactants.

Also mixtures of several anionic surfactants, for example mixtures of an alpha-olefin sulfate and a sulfo succinate, preferably in the relation of from about 1:3 to 3:1, or an ether sulfate and a polyethercarboxylic acid or an alkylamidoethercarboxylic acid can be used.

The concentration of anionic surfactant is preferably from about 0.5 to 10 wt. %, more preferably from about 1 to 5 wt. %.

Other examples of suitable non-ionic surfactants are e.g. alkylpolyglucosides, sorbitan esters such as polyethyleneglycol-sorbitan stearate, fatty acid polyglycol ester or also ester of fatty acid and mixed-polymerized polyglycol from ethylene oxide and propylene oxide, as they are on the market, for example, under the trade name "Pluronics®".

Further an additionally applicable surfactant is amine oxide. Such amine oxides belong to the state of the art for a long time, for example $C_{12-18}$ alkyldimethylamine oxide such as lauryldimethylamine oxide, $C_{12-18}$ alkylamidopropylamide oxide or alkylamidoethylamine oxides, $C_{12-18}$ alkyldi(hydroxyethyl) amine oxide or alkyldi(hydroxypropyl) amine oxide or also amine oxides which have groups of ethylene oxides and/or propylene oxides in their alkyl chain. Suitable amine oxides are on the market, for example under the trade name of "Ammonyx®", "Aromox®" or "Genaminox®".

Further optical surfactant constituents are fatty acid-mono and dialkanolamide, like coco fatty acid-monoethanolamide and myristic acid-monoisopropanolamide.

Examples of suitable amphoteric or zwitter-ionic surfactants include, in particular, well known betaines such as fatty acid-amidoalkylbetaine and sulfobetaine, for example laurylhydroxysulfobetaine; long-chained alkylamino acids such as cocoaminoacetate, cocoaminopropionate, sodium cocoamphopropionate and sodium cocoamphoacetate are listed as suitable examples.

Examples of suitable cationic surfactants include long-chained quaternized ammonium compounds, which can be used alone or in combination, like cetyltrimethylammonium chloride, dimethylstearylammonium chloride, trimethylacetylammonium bromide, stearyltrimethylammonium chloride, dimethylstearylbenyzlammonium chloride, bnezyltetradecyldimethylammonium chloride, dimethyl dihydrogenated-tallow ammonium chloride, lauryldimethylbenzylammonium chloride, behenyltrimethylammonium chloride, lauryltrimethylammonium chloride, tris-(oligooxy-ethyl)alkylammonium phosphate, cetylpridinium chloride, etc.

The composition of the present invention can contain also optional preservative agents such as oils and fats. Examples include sun flower oil, almond oil, peach kernel oil, wheat germ oil, macadamia nut oil, night Evening Primrose oil, jojoba oil, castor oil, or also olive or soybean oil, lanolin and its derivatives, likewise mineral oils such as paraffin oil and Vaseline® and a mixture thereof.

If the composition of the present invention is present in the form of an emulsion, the composition may comprise generally used emulsifying agents. The composition according to the present invention can comprise long-chained fatty acids. As fatty acids, $C_{10-24}$, particularly $C_{12-22}$ fatty acids are preferable, and they can be incorporated in an amount of from about 0.5 to 15 wt. %, preferably from about 1 to 10 wt. %, calculated based on the whole composition. Behenic acid and stearic acid are particularly suitable; however, other fatty acids, for example myristic aicd, palmitic acid, oleic acid or also mixtures of natural or synthetic fatty acids such as coco-fatty acid can be incorporated.

The hair dye compositions of the present invention may additionally include a thickener at a level of from about 0.05% to about 20%, preferably from about 0.1% to about 10%, more preferably from about 0.5% to about 5% by weight of the composition. Thickening agents suitable for use in the compositions herein are selected from oleic acid, cetyl acohol, oleyl alcohol, sodium chloride, cetearyl alcohol, stearyl alcohol.

Water is the preferred diluent for the preferred compositions according to the present invention. However, the compositions according to the present invention may also include one or more solvents as additional materials. Generally, solvents suitable for use in the dye compositions of the present invention are selected to be miscible with water and are not detrimental to the hair and/or scalp. Solvents suitable for use as additional diluents herein include $C_1$–$C_{20}$ mono- or polyhydric alcohols and their ethers, glycerine, with monohydric and dihydric alcohols and their ethers being preferred. In these compounds, alcoholic residues containing 2 to 10 carbon atoms are preferred. Thus, a preferred group includes ethanol, isopropanol, n-propanol, butanol, n-pentanol, propylene glycol, ethylene glycol monoethyl ether, 1,2-hexanediol, butoxyethanol, phenoxyethanol, benzyl alcohol, propylene carbonate and mixtures thereof. Further preferred solvents for the composition of the present invention are 1,2- and 1,3-propanediol, 1-methoxy-2-propanol, 1-ethoxy-2-propanol, 1,3- and 1,4-butanediol, diethylene glycol and its monomethyl and monoethyl ether as well as dipropyleneglycol and its monomethyl and monoethyl ether. The proportion of these diols is preferably from about 0.5 and 30 wt. %, more preferably from about 1 to 15 wt. %, even more preferably from about 5 to 10 wt. % of the whole composition. In addition to these $C_{3-6}$ alkanediols or their ethers, monoalcohols such as ethanol, 1-propanol and 2-propanol; polyalcohols such as glycerine and hexanetriol; ethylcarbitol; benzyl alcohol; benzyloxyethanol; propylene carbonate (4-methyl-1,3-dioxan-2-on); n-alkylpyrrolidone; and urea are also suitable and can be used.

Water is the preferred principal diluent in the preferred compositions according to the present invention. Principal diluent, as defined herein, means, that the level of that diluent present is higher than the total level of any other diluents.

The solvent is present at a level preferably of from about 0.01% to about 99%, more preferably from about 0.05% to about 50%, even more preferably at least from about 0.1% to 15%, even more preferably from about 0.2% to 5% based on the whole composition.

The hair dye composition of the present invention can be prepared in a conventional manner into a one-part composition, a two-part composition having a first component part containing an alkaline agent and a second component part containing an oxidizing agent, or a three-part composition having, in addition to these two component parts, a powdery oxidizing agent such as persulfate. The direct dye (1) may be incorporated in either one or both of these component parts of the two-part or three-part composition. When the hair dye composition of the present invention is a one-part type, it is applied to the hair directly, while the two- or three-part type is applied to the hair after mixing these parts upon hair dyeing.

Typically, the first composition comprises the azo dye represented by formula (1) and an alkaline agent in an aqueous medium with a pH of from about 8 to 12. The second composition comprises hydrogen peroxide in a slightly acidic aqueous medium. The third composition comprises a persulfate and inert powder to form agglomerates. Small amounts of the third composition are added into the mixture of the first and the second composition.

No particular limitation is imposed on the form of the hair dye composition of the present invention. Examples include powder, transparent liquid, emulsion, cream, gel, paste, aerosol, and aerosol foam. It preferably has a viscosity of about 2000 to 100000 mPa·s in the stage of application to the hair (after mixing of all the component parts when the composition is a two-part or three-part type). The viscosity is measured at 20° C. by using a Brookfield rotary viscosimeter with a spindle No. 5 at 5 rpm.

The azo dye (1) of the present invention may be used for dyeing human or animal hair. Such hair dyeing method comprises applying the azo dye (1) to the hair, rinsing the hair after the dyeing, and drying the hair after the rinsing.

EXAMPLES

The present invention will be described in greater detail by referring to the examples and comparative examples. The following examples further describe and demonstrate embodiments of the present invention. The examples are given solely for the purpose of illustration and are not to be construed as limitations of the present invention.

Specific synthetic examples of the compound represented by general formula (1) in accordance with the preferred embodiments of the invention will be described below.

Synthesis of Listed Compound D-6

The compound was synthetically prepared according to the following scheme.

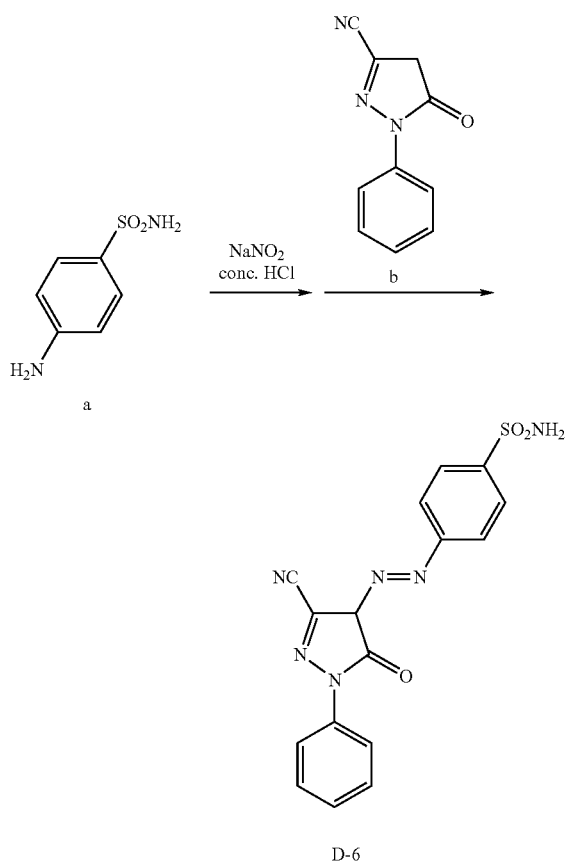

D-6

Sulfanilamide (intermediate a, 25.8 g; 0.150 mol) and conc. hydrochloric acid (45.0 ml; 0.525 mol) were added to 150 ml of water, and the resulting mixture was stirred for 30 min under cooling in an ice water bath. Sodium nitrite solution (10.4 g; 0.150 mol in 20 ml of water) was added dropwise over 20 min. The resulting mixture was stirred for 1 hr. under cooling in the ice water bath.

3-Cyano-1-phenyl-5-pyrazolone (intermediate b, 27.8 g; 0.150 mol) was added to 200 ml of methanol. After stirring for a few minutes, sodium acetate (43.1 g; 0.525 mol) and 50 ml of water was added to the mixture and the resulting mixture was stirred under cooling in the ice water bath for 20 min. To this mixture, the diazonium salt solution prepared above was added gradually over 1 hr. After stirring under cooling for one and a half hours, the precipitate was filtered off and washed with water, and dried to form 55.2 g of the crude product of D-6.

The crude product and triethylamine (20.9 ml; 0.150 mol) were added to 260 ml of methanol and the resulting mixture was refluxed for 20 min while stirring. After short cooling to stop refluxing, the hot mixture was filtered through a Celite pad and washed with 50 ml of methanol. The filtrate was stirred under cooling in a water bath. To the mixture, diluted hydrochloric acid (12.8 ml of conc. hydrochloric acid was diluted with 25 ml of water) was added dropwise over about 20 min. After stirring for 1 hr., the precipitate was filtered off and washed with 140 ml of methanol. The wet cake of D-6 was added to 200 ml of acetonitrile and the resulting mixture was refluxed for 30 min. while stirring. After cooling to room temperature while stirring, the precipitate was filtered off, washed with 80 ml of acetonitrile, and dried to form 50.6 g of D-6 as an orange crystal (91.6%) $^1$H NMR (DMSO-$d_6$, ppm) 7.95–7.85 (m, 6H), 7.53 (t, 2H), 7.42 (brs, 2H), 7.35 (t, 1H)

Synthesis of Listed Compound D-14

The compound was synthetically prepared according to the following scheme.

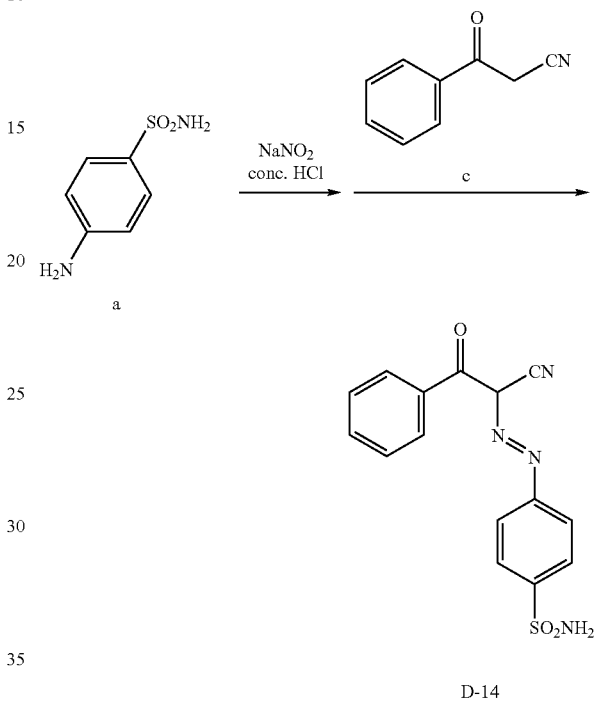

D-14

Sulfanilamide (intermediate a, 25.8 g; 0.150 mol) and conc. hydrochloric acid (45.0 ml; 0.525 mol) were added to 150 ml of water, and the resulting mixture was stirred for 30 min under cooling in an ice water bath. Sodium nitrite solution (10.4 g; 0.150 mol in 20 ml of water) was added dropwise over 20 min. The resulting mixture was stirred for 1 hr. under cooling in the ice water bath.

Benzoylacetonitrile (intermediate c, 21.8 g; 0.150 mol) was added to 200 ml of methanol. After stirring for a few minutes, sodium acetate (43.1 g; 0.525 mol) and 50 ml of water was added to the mixture and the resulting mixture was stirred under cooling in an ice water bath for 20 min. To this mixture, the diazonium salt solution prepared above was added gradually over 1 hr. After stirring under cooling for one and a half hrs., the precipitate was filtered off and washed with water, and dried to form 47.7 g of the crude product of D-14.

The crude product and triethylamine (24.3 ml; 0.174 mol) were added to 250 ml of methanol and the resulting mixture was refluxed for 20 min. while stirring. After short cooling to stop refluxing, the hot mixture was filtered through a Celite pad and washed with 50 ml of methanol. To the stirring filtrate under cooling in the water bath, diluted hydrochloric acid (15.0 ml of conc. hydrochloric acid was diluted with 30 ml of water) was added dropwise over 30 min. After stirring for 1 hr., the precipitate was filtered off, washed with 100 ml of methanol and 100 ml of water. The wet cake of D-14 was added to 150 ml of acetonitrile and the resulting mixture was refluxed for 30 min. while stirring. After cooling to room temperature while stirring, the precipitate was filtered off, washed with 100 ml of acetonitrile, and dried to form 46.7 g of D-14 as a yellow crystal (94.8%).

$^1$H NMR (DMSO-$d_6$, ppm) 12.53 (brs, 1H), 7.90 (dd, 2H), 7.81 (d, 2H), 7.66 (t, 1H), 7.56 (t, 2H), 7.48 (d, 2H), 7.30 (brs, 2H)

Synthesis of Listed Compound D-21

The compound was synthetically prepared according to the following scheme.

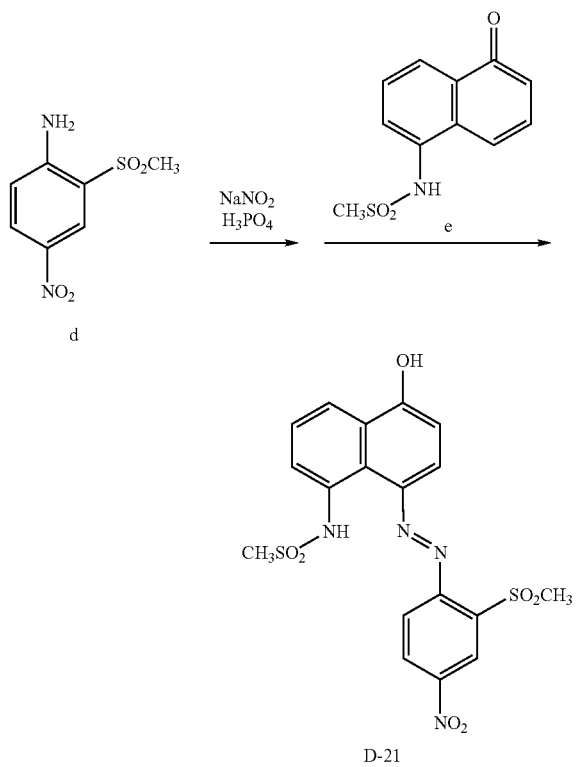

D-21

2-Methylsulfonyl-4-nitroaniline (intermediate d, 13.0 g; 60.0 mmol) was added to 50 ml of phosphoric acid, and the resulting mixture was vigorously stirred under cooling in ice water. Sodium nitrite (4.00 g; 58.0 mmol) in crystal form was added gradually over 20 min. to the mixture, which was stirred for 1 hr.

5-Methylsulfonylamino-1-naphthol (intermediate e, 11.9 g; 50.0 mmol) was added to methanol (100 ml), and the resulting mixture was stirred under cooling in an ice water bath, to which was then gradually added the diazo solution prepared above in a divided manner over 30 min. The temperature of the reaction mixture was maintained under 10° C. After stirring while cooling for one hour and stirring at room temperature for another one hour, 100 ml of water was added dropwise to the reaction mixture. After stirring for 30 min., the precipitate was filtered off, and washed with 150 ml of water. After drying overnight at about 40° C., the crude product of D-21 was obtained (24.7 g).

The crude product and triethylamine (16.8 ml; 0.120 mol) were added to 400 ml of methanol and the resulting mixture was refluxed for 40 min. while stirring. After short cooling to stop refluxing, the hot mixture was filtered through a Celite pad and washed with 100 ml of methanol. To the stirring filtrate under cooling in a water bath, diluted hydrochloric acid (10.4 ml of conc. hydrochloric acid was diluted with 30 ml of water) was added dropwise over about 30 min. After stirring for 30 min., the precipitate was filtered off, and washed with 100 ml of methanol. The wet cake of D-21 was added to 100 ml of acetonitrile and the resulting mixture was refluxed for 30 min. while stirring. After cooling to room temperature while stirring, the precipitate was filtered off, washed with 50 ml of acetonitrile, and dried to form 10.5 g of D-21 (45.2%).

$^1$H NMR (DMSO-$d_6$, ppm) 12.8 (brs, 1H), 8.60 (d, 1H), 7.42 (brs, 1H), 8.20 (brd, 1H), 7.92 (d, 1H), 7.83 (d, 1H), 7.71 (d, 1H), 7.51 (t, 1H), 6.72 (brd, 1H), 3.49 (s, 3H), 3.20 (s. 3H)

1) Examples of Dyeing Performance of Dyestuffs

The dyes listed in Tables 1a and 1b were dissolved into a mainly aqueous formulation containing alkaline peroxide and applied in the form of a composition having General Formulation A to goat and human hair.

| General Formulation A | |
|---|---|
| Dyestuff of formula (1) | 0.2 g |
| Benzyl Alcohol | 5.0 g |
| Sodium Lauryl Suplhate | 0.01 g |
| Ammonium Hydroxide (25%) | 5.0 g |
| Hydrogen Peroxide (50%) | 6.0 g |
| Water | up to 100 g |
| pH | 10.0 |

The dye mixture was applied to undamaged white goat hair and to undamaged human blond hair at 50° C. for 15 min. 1.5–2.0 g of General Formulation A was applied per gram of hair. After the dyeing time (approximately 15 to 30 minutes) was completed, the tresses were rinsed with water, shampooed, and then dried. The color of the tresses was then recorded. L, a and b values of the tresses before and after the colouring treatment were measured by a Minolta colour-measuring instrument and the value of delta E, which is a known measure for the chroma, was calculated according to the well-known equation: $\Delta E=(\Delta L^2+\Delta a^2+\Delta b^2)^{1/2}$ for each example (this will apply equally to every example hereinafter).

The results are shown in Table 1a (Goat Hair) and Table 1b (Human Hair.)

TABLE 1a

Color on Undamaged White Goat Hair

| Dye Example | Color of Dyed Hair | L | a | b | Delta E |
|---|---|---|---|---|---|
| D-2 | Bright Pink/Magenta | 51 | 44 | −10 | 60 |
| D-4 | Intense Pink | 48 | 51 | −2 | 65 |
| D-5 | Pink | 48 | 42 | −2 | 58 |
| D-6 | Bright Yellow | 81 | 0 | 72 | 58 |
| D-7 | Intense Gold | 76 | 14 | 74 | 62 |
| D-8 | Bright Yellow | 84 | −3 | 63 | 49 |
| D-9 | Bright Yellow | 83 | −2 | 57 | 44 |
| D-10 | Bright Gold Yellow | 79 | 3 | 68 | 54 |
| D-14 | Intense Yellow | 84 | −11 | 65 | 52 |
| D-15 | Orange/Gold | 76 | 13 | 62 | 50 |
| D-16 | Bright Yellow | 82 | 1 | 66 | 52 |
| D-17 | Bright Gold | 78 | 7 | 71 | 57 |
| D-18 | Yellow-Orange | 75 | 18 | 66 | 56 |
| D-19 | Intense Yellow | 82 | −4 | 66 | 52 |
| D-21 | Intense Cyan | 37 | −17 | −18 | 60 |
| D-22 | Cyan | 44 | −4 | −4 | 45 |

TABLE 1a-continued

Color on Undamaged White Goat Hair

| Dye Example | Color of Dyed Hair | L | a | b | Delta E |
|---|---|---|---|---|---|
| D-23 | Blue | 44 | 9 | −22 | 56 |
| D-24 | Cyan | 56 | −11 | −16 | 44 |
| D-25 | Ash Blue | 38 | 8 | −5 | 51 |
| D-27 | Bright Blue | 37 | 10 | −26 | 63 |
| D-29 | Bright Yellow | 80 | 3 | 70 | 56 |

TABLE 1b

Color on Undamaged Human Blonde Hair

| Dye Example | Color of Dyed Hair | L | a | b | Delta E |
|---|---|---|---|---|---|
| D-2 | Pink/Red | 39 | 21 | 8 | 18 |
| D-4 | Pink | 33 | 31 | 9 | 28 |
| D-5 | Light Pink | 42 | 21 | 12 | 17 |
| D-6 | Bright Yellow | 57 | 7 | 41 | 26 |
| D-7 | Intense Gold | 53 | 10 | 44 | 28 |
| D-8 | Bright Yellow | 58 | 6 | 30 | 18 |
| D-9 | Bright Yellow | 56 | 6 | 30 | 16 |
| D-10 | Bright Gold Yellow | 56 | 6 | 36 | 22 |
| D-14 | Intense Yellow | 56 | 4 | 35 | 21 |
| D-15 | Orange/Gold | 54 | 9 | 36 | 21 |
| D-16 | Bright Yellow | 60 | 3 | 19 | 25 |
| D-17 | Bright Gold | 56 | 6 | 36 | 22 |
| D-18 | Yellow-Orange | 62 | 6 | 34 | 23 |
| D-19 | Intense Yellow | 64 | 4 | 26 | 20 |
| D-21 | Intense Cyan | 35 | −18 | −4 | 33 |
| D-22 | Olive Brown | 36 | −2 | 7 | 15 |
| D-23 | Ash Blue | 36 | 2 | 1 | 17 |
| D-24 | Olive Brown | 43 | −6 | 7 | 16 |
| D-25 | Ash Blue | 34 | 6 | 9 | 11 |
| D-27 | Blue | 32 | 2 | −4 | 23 |
| D-29 | Bright Yellow | 54 | 7 | 35 | 20 |

2) Comparison with Anionic Dyes

The performance of dyes of the embodiments of the invention were compared with that of dyes not covered by the invention. Thus dyes D-6, A* and B* were used in general Formulation A and applied to undamaged white goat hair and undamaged human blonde hair for 15 min. at 50° C. (see Tables 2a and 2b).

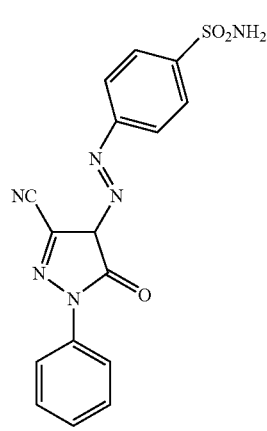

D-6

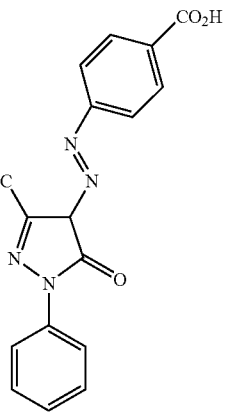

A*

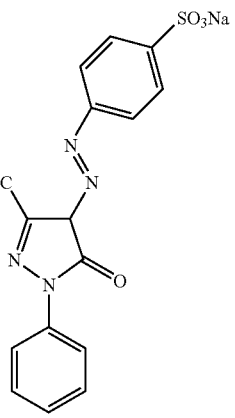

B*

TABLE 2a

Color uptake on undamaged white goat hair

| Dye | Color | L | a | b | Delta E |
|---|---|---|---|---|---|
| D-6 | Very Intense Yellow | 81 | 0 | 72 | 59 |
| A* | Pale Yellow | 86 | −6 | 41 | 42 |
| B* | Pale Yellow | 85 | −5 | 42 | 43 |

*Comparative Example

TABLE 2b

Color uptake undamaged Blonde human hair

| Dye | Color | L | a | b | Delta E |
|---|---|---|---|---|---|
| D-6 | Very Intense Gold | 57 | 7 | 41 | 26 |
| A* | Pale Yellow | 55 | 7 | 26 | 13 |
| B* | Pale Yellow | 55 | 6 | 26 | 13 |

*Comparative Example

Furthermore a comparison of the dyeing performance of dyes D-14 and C* was carried out using General Formulation A and the same dyeing method as described above. The results are shown in Tables 3a and 3b.

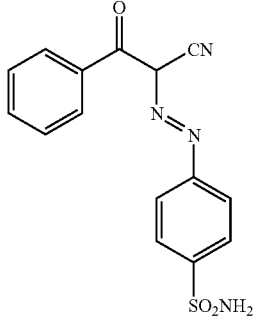

D-14

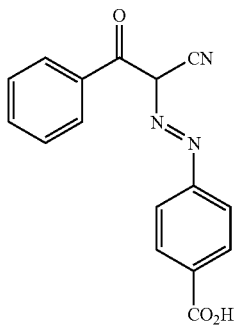

C*

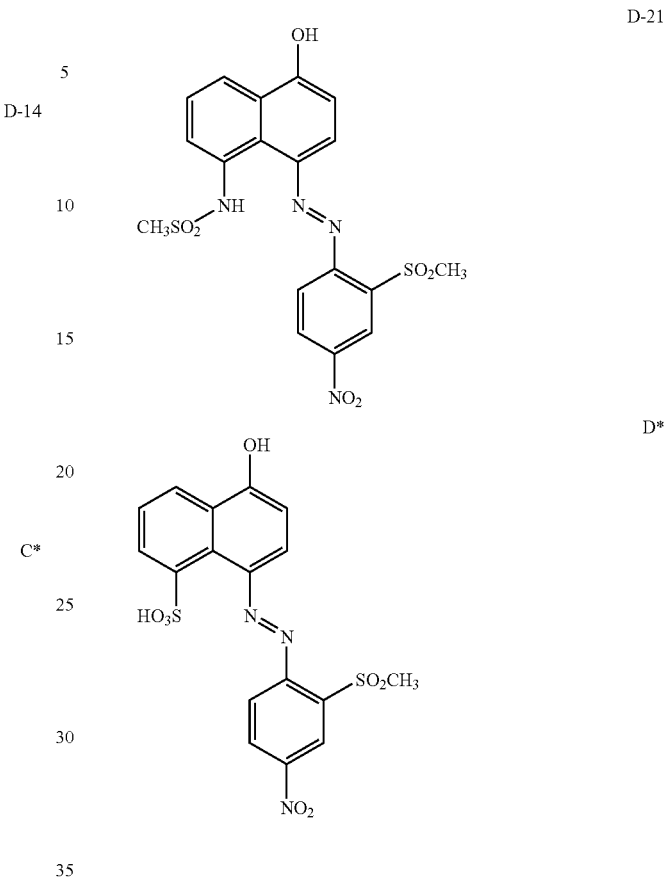

TABLE 3a

Color uptake on undamaged white goat hair

| Dye | Color | L | a | b | Delta E |
|---|---|---|---|---|---|
| D-14 | Very Intense Yellow | 84 | −11 | 65 | 52 |
| C* | Pale Yellow | 87 | −6 | 31 | 19 |

*Comparative Example

TABLE 3b

Color uptake undamaged Blonde human hair

| Dye | Color | L | a | B | Delta E |
|---|---|---|---|---|---|
| D-14 | Very Intense Gold | 56 | 4 | 35 | 21 |
| C* | Pale Yellow | 52 | 6 | 25 | 12 |

*Comparative Example

Similarly, the performance of D-21 and D* were also compared in General Formulation A. The results are summarised in Tables 4a and 4b.

TABLE 4a

Color uptake on undamaged white goat hair

| Dye | Color | L | a | B | Delta E |
|---|---|---|---|---|---|
| D-21 | Intense Cyan | 37 | −17 | −18 | 60 |
| D* | Pale Cyan | 65 | −13 | 2 | 23 |

*Comparative Example

TABLE 4b

Color uptake on undamaged Blonde human hair

| Dye | Color | L | a | B | Delta E |
|---|---|---|---|---|---|
| D-21 | Intense Cyan | 35 | 18 | −4 | 33 |
| D* | Pale Blonde | 51 | 2 | 19 | 7 |

*Comparative Example

In all cases, the dyes containing sulfo or carboxylic groups provided much weaker color on hair than the analogous non-anionic dyestuff. Clearly, the presence of a —COOH or a —SO$_3$H group, drastically reduces dyeing performance and thus these groups are excluded from the invention.

3) Examples of Fading from Washing.

In order to assess the performance of the dyes of general formula I as defined, in terms of resistance to fading from washing, Dye D-5 was compared with a diazo dye containing a cationic group E*.

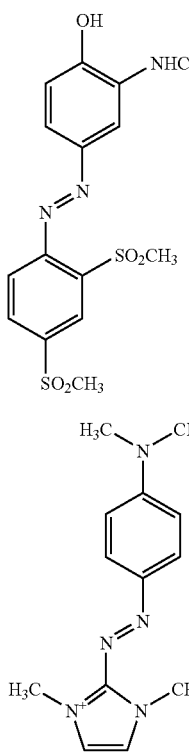

* Comparative Example

Using the same formulation as described above (General Formulation A), the dyes were applied for 15 min. at 50° C. to damaged (permed) white goat hair. After the dyeing process was complete, the tresses were washed and dried and the color noted. The tresses were then put through a wash fade protocol, to measure the resistance to shampooing.

The washing protocol consisted of applying 0.1 g of shampoo per 1 g of hair and milking into the hair for 30 seconds followed by rinsing the tresses for 30 seconds with 40° C. water. This process was repeated 20 times. The tresses were then dried and the change in color measured as a delta E value, using the Minolta Colorimeter. The results are shown in Table 4.

TABLE 4

Fading by washing of Dye of the Invention Examples compared to Comparative Examples

| Dye Example | Treatment | L | A | b | ΔE fade |
|---|---|---|---|---|---|
| D-5 | Initial | 33 | 55 | 0 | |
| D-5 | 20 washes | 34 | 57 | 0 | 3 |
| Cationic Direct Dye E* | Initial | 32 | 58 | 19 | |
| Cationic Direct Dye E* | 20 Washes | 54 | 58 | 4 | 27 |

*Comparative Examples

Clearly, the presence of a cationic group drastically reduces the durability of the dyestuffs to shampooing on damaged hair. Thus, cationic substituents are excluded from the invention.

4) pka Values of Some Illustrated Dyes.

The pka values of some dyes in accordance with the preferred embodiments of the present invention have been measured as described in the specification. The values are shown below:

| Dyes | pka |
|---|---|
| D-6 | 4.2 |
| D-7 | 4.6 |
| D-14 | 5.82 |
| D-15 | 4.36 |
| D-17 | 5.92 |
| D-18 | 2.86 |
| D-21 | 4.32 |
| D-22 | 6.34 |
| D-24 | 5.09 |
| D-25 | 6.5 |
| D-26 | 7.1 |

The invention claimed is:

1. A hair dyeing composition comprising a dissociative azo dye represented by formula (1)

$$A-N=N-B \quad (1)$$

wherein "A" represents a phenyl or naphthyl group which may be substituted; "B" represents an atomic group containing a dissociative proton selected from groups (B-1) to (B-12) binding via symbol ** to the azo group consisting of:

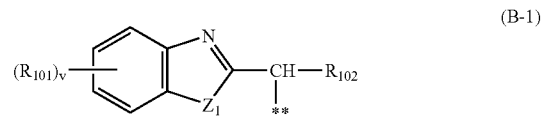

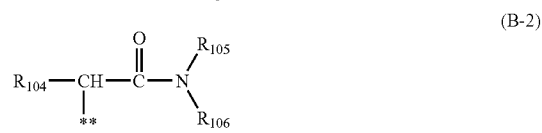

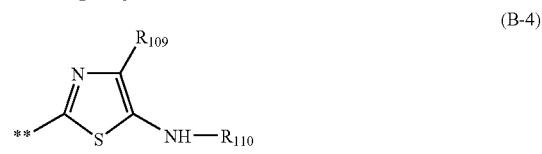

-continued

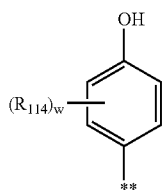
(B-6)

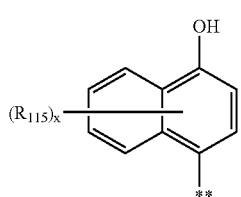
(B-7)

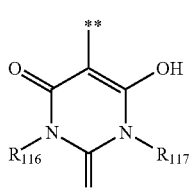
(B-8)

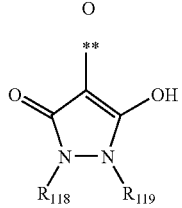
(B-9)

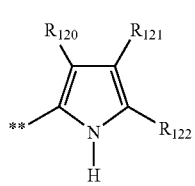
(B-10)

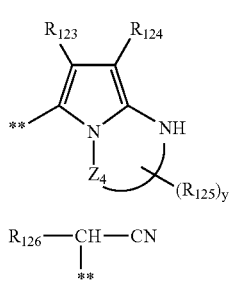
(B-11)

$R_{126}$—CH—CN (B-12)

wherein $R_{101}$ represents a halogen atom, alkyl group, aryl group, hetero-ring group, cyano group, alkoxy group, amino group (including anilino group), acylamino group, alkylsulfonylamino group, arylsulfonylamino group, alkylthio group, arylthio group, sulfamoyl group, alkylsulfonyl group, or carbamoyl group, $R_{102}$ and $R_{104}$ each independently represent cyano group, alkylsulfonyl group, arylsulfonyl group, acyl group, alkoxycarbonyl group, aryloxycarbonyl group, or carbamoyl group, $Z_1$ represents oxygen atom, sulfur atom, or —N($R_{103}$—, wherein $R_{103}$ represents hydrogen atom, alkyl group, aryl group or hetero-ring group, "v" represents an integer of 0 to 4, wherein several $R_{101}$ groups may be the same or different;

$R_{105}$ and $R_{106}$ independently represent a hydrogen atom, alkyl group, aryl group, or hetero-ring group;

$R_{107}$ represents a hydrogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, or carbamoyl group; $Z_2$ and $Z_3$ independently represent —C($R_{108}$)= or —N=; $R_{108}$ represents alkyl group, aryl group, hetero-ring group, alkylthio group, arylthio group, alkoxycarbonyl group, or carbamoyl group, wherein if $Z_2$ and $Z_3$ both represent —C($R_{108}$)=, two $R_{108}$ groups may be the same or different or may bind together to form a carbon ring or a hetero-ring;

$R_{109}$ represents an alkyl group, aryl group or hetero-ring group, and $R_{110}$ represents a hydrogen atom, alkyl group, aryl group, hetero-ring group, acyl group, alkylsulfonyl group or arylsulfonyl group, $R_{111}$ represents a hydrogen atom, alkyl group, aryl group, alkoxy group, amino group (including anilino group), alkoxycarbonyl group, cyano group, acylamino group, or carbamoyl group; $R_{112}$ represents hydrogen atom, alkyl group, aryl group, or hetero-ring group; $R_{113}$ represents hydroxy group or amino group, $R_{114}$ and $R_{115}$ represent a halogen atom, alkyl group, aryl group, nitro group, aryloxy group, anilino group, acylamino group, alkoxycarbonylamino group, aminocarbonylamino group, alkylsulfonylamino group, arylsulfonylamino group, alkylthio group, arylthio group, hetero-ring thio group, alkoxycarbonyl group, or carbamoyl group; "w" represents an integer of from 1 to 4, wherein several $R_{114}$ groups in the number "w" may be the same or different; "x" represents an integer of from 0 to 6, wherein several $R_{115}$ groups in the number "x" may be the same or different, $R_{116}$, $R_{117}$, $R_{118}$, and $R_{119}$ independently represent an alkyl group or aryl group, $R_{120}$ and $R_{121}$ independently represent an alkyl group, aryl group, hetero-ring group, cyano group, alkylsulfonyl group, arylsulfonyl group, alkoxycarbonyl group, or carbamoyl group; $R_{122}$ represents a hydrogen atom, alkyl group, aryl group, hetero-ring group, acylamino group, alkylsulfonylamino group, or arylsulfonylamino group, $R_{123}$ and $R_{124}$ independently represent an alkyl group, aryl group, hetero-ring group, cyano group, alkylsulfonyl group, arylsulfonyl group, alkoxycarbonyl group, or carbamoyl group; $Z_4$ represents a non-metal atomic group forming a 5-membered or 6-membered ring, together with the two nitrogen atoms and one carbon atom, $R_{125}$ represents an alkyl group, aryl group, alkoxy group, amino group, acylamino group, alkylsulfonylamino group, arylsulfonylamino group, alkylthio group, arylthio group, acyl group, alkoxycarbonyl group, or carbamoyl group; "y" represents an integer of from 0 to 2, when $Z_4$ forms a 5-membered ring; and "y" represents an integer of from 0 to 3, when $Z_4$ forms a 6-membered ring, and $R_{126}$ represents an alkyl group, aryl group, cyano group or alkoxy carbonyl group;

and wherein $R_{101}$ to $R_{126}$ in formulas (B-1) to (B-12) may have additional substituents; and, with the proviso "A" and "B" are free of sulfo, carboxyl and quaternary ammonium groups.

2. The hair dyeing composition according to claim 1, wherein the structure of the azo dye is represented by any one of DS-1 to DS-9:

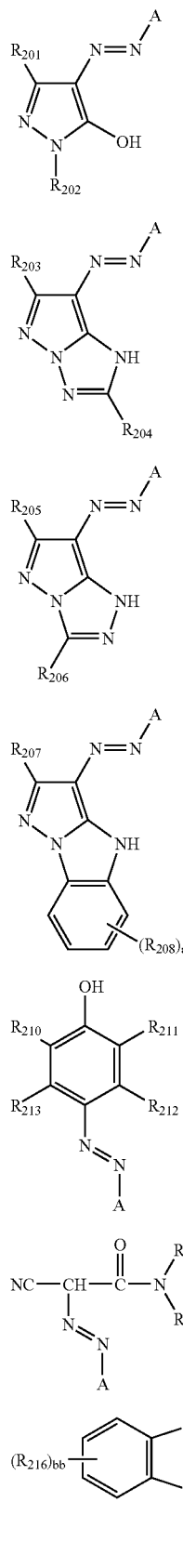

wherein "A" has the same meaning as defined in claim 1;

R$_{201}$ represents a hydrogen atom, alkyl group, aryl group, alkoxy group, amino group (including anilino group), alkoxycarbonyl group, cyano group, acylamino group, or carbamoyl group; R$_{202}$ represents a hydrogen atom, alkyl group, aryl group, or hetero-ring group;

R$_{203}$, R$_{205}$ and R$_{207}$ represent a hydrogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, or carbamoyl group; R$_{204}$ represents an alkyl group, aryl group, or hetero-ring group;

R$_{206}$ represents an alkyl group, aryl group, hetero-ring group, alkyithjo group, arylthio group, alkoxycarbonyl group, or carbamoyl group;

R$_{208}$ represents a halogen atom, alkyl group, aryl group, hetero-ring group, alkoxy group, aryloxy group, amino group (including anilino group), acylamino group, alkylsulfonylamino group, arylsulfonylamnio group, alkylthio group, arylthio group, alkylsulfonyl group, arylsulfonyl group, alkoxycarbonyl group, or carbamoyl group; "aa" represents an integer of from 0 to 4, provided that aa is 2 to 4, the R$_{208}$ groups may be the same or different;

R$_{210}$ represents a hydrogen atom, halogen atom, alkyl group, aryl group, acylamino group, alkoxycarbonyl group, aininocarbonylamino group, alkylsulfonylamino group, arylsulfonylamino group, alkoxycarbonylamino group, or earbamoyl group; R$_{211}$ represents a halogen atom, alkyl group, aryl group, acylamino group, alkoxycarbonyl group, aminocarbonylamino group, alkylsulfonylamino group, arylsulfonylamino group, alkoxycarbonylamino group, or carbamoyl group; R$_{212}$ and R$_{213}$ independently represent a hydrogen atom, halogen atom, alkyl group, alkoxy group, or acylamino group;

R$_{214}$ and R$_{215}$ independently represent a hydrogen atom, alkyl group, aryl group, or hetero-ring group;

R$_{216}$ represents a halogen atom, alkyl group, aryl group, hetero-ring group, cyano group, alkoxy group, amino group (including anilino group), acylamino group, alkylsulfonylamino group, arylsulfonylamino group, alkylthio group, arylthio group, sulfamoyl group, alkylsulfonyl group, or carbamoyl group; Z$_5$ represents an oxygen atom, sulfur atom, or —N(R$_{217}$)—, where R$_{217}$ represents a hydrogen atom, alkyl group, aryl group, or hetero-ring group; "bb" represents an integer of from 0 to 4; provided that if "bb" is a plural number, the $R_{216}$ groups in the number "bb" may be the same or different;

$R_{218}$ represents a hydrogen atom, halogen atom, alkyl group, aryl group, acylamino group, alkylsulfonylamino group, arylsulfonylamino group, alkoxycarbonylamino group, aminocarbonylamino group, carbamoyl group, or sulfamoyl group; $R_{219}$ and $R_{223}$ independently represent a hydrogen atom, halogen atom, acylamino group, alkoxycarbonylamino group, aminocarbonylamino group, alkylsulfonylamino group, or arylsulfonylamino group; $R_{219}$, $R_{221}$, and $R_{222}$ independently represent a hydrogen atom, chlorine atom, bromine atom, alkyl group, or acylamino group; and $R_{224}$ represents an alkyl group, aryl group, cyano group or alkoxycarbonyl group wherein $R_{201}$ to $R_{224}$ in formulas DS-1 to DS-9 may have additional substituents.

3. The hair dyeing composition according to claim 1, wherein the azo dye of formula (1) is present in an amount of from about 0.0001 to 20% by weight, based on the whole composition.

4. The hair dyeing composition according to claim 1, further comprising at least one direct dye other than the azo dye of general formula (1) andlor at least one oxidative dye.

5. The hair dyeing composition as claimed in claim 4, wherein the total amount of the dyes present in said composition is from about 0.00 1% to 20% by weight, based on the whole composition.

6. The hair dyeing composition according to claim 1, further comprising an alkaline agent in an amount of from about 0.01% to 20% by weight, based on the whole composition.

7. The hair dyeing composition as defined in claim 1, being a one part composition, a two part composition or a three part composition, wherein the two part composition comprises a first part containing an alkaline agent and a second part containing an oxidative agent, and wherein the three part composition contains the first and second parts and additionally a third part containing a powdery oxidizing agent, wherein in each of the said composition the direct dye having formula (1) is contained in either one of the respective parts or in each part.

8. A method for dyeing human or animal hair, comprising applying a composition comprising an azo dye represented by formula (1) to the hair, rinsing the hair after completion of the dyeing and drying the hair:

$$A\text{-}N\!=\!N\text{—}B \qquad (1)$$

wherein "A" represents a phenyl or naphthyl group which may be substituted; "B" represents an atomic group containing a dissociative proton selected from groups (B-1) to (B-12) binding via symbol ** to the azo groun consisting of:

-continued

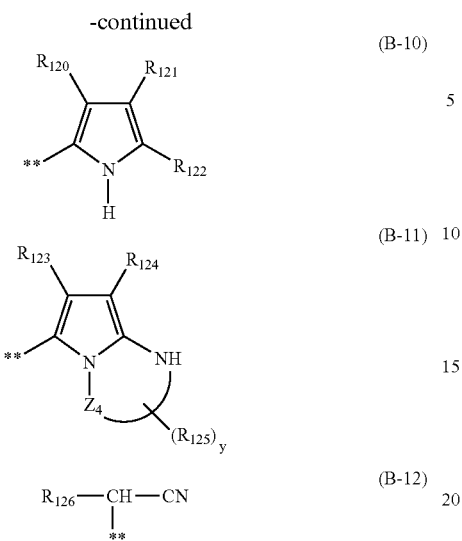

(B-10)

(B-11)

(B-12)

wherein $R_{101}$ represents a halogen atom, alkyl group, aryl group, hetero-ring group, cyano group, alkoxy group, amino group (including anilino group), acylamino group, alkylsulfonviamino group, arvisulfonviamino group, alkvlthio group, arvlthio group, sulfamoyl group, alkylsulfonvi group, or carbamoyl group, $R_{102}$ and $R_{104}$ each independently represent cyano group, alkylsulfonyl group, arylsulfonyl group, acyl group, alkoxycarbonyl group, aryloxycarbonyl group, or carbamoyl group, $Z_1$ represents oxygen atom, sulfur atom, or —N($R_{103}$)—, wherein $R_{103}$ represents hydrogen atom, alkyl group, aryl group or hetero-ring group, "v" rep resents an integer of 0 to 4, wherein several $R_{101}$ groups may be the same or different;

$R_{105}$ and $R_{106}$ independently represent a hydrogen atom, alkyl group, aryl group, or hetero-ring group;

$R_{107}$ represents a hydrogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, or carbamoyl group; $Z_2$ and $Z_3$ independently represent —C($R_{108}$)= or —N=; $R_{108}$ represents alkyl group, aryl group, hetero-ring group, alkylthio group, arylthio group, alkoxycarbonyl group, or carbamoyl group, wherein if $Z_2$ and $Z_3$ both represent —C($R_{108}$)=, two $R_{108}$ groups may be the same or different or may bind together to form a carbon ring or a hetero-ring;

$R_{109}$ represents an alkyl group, aryl group or hetero-ring group, and $R_{110}$ represents a hydrogen atom, alkyl group, aryl group, hetero-ring group, acyl group, alkylsulfonyl group or arylsulfonyl group, $R_{111}$ represents a hydrogen atom, alkyl group, aryl group, alkoxy group, amino group (including anilino group), alkoxycarbonyl group, cyano group, acylamino group, or carbamoyl group; $R_{112}$ represents hydrogen atom, alkyl group, aryl group, or hetero-ring group; $R_{113}$ represents hydroxy group or amino group, $R_{114}$ and $R_{115}$ represent a halogen atom, alkyl group, aryl group, nitro group, aryloxy group, anilino group, acylamino group, alkoxycarbonylamino group, aminocarbonylamino group, alkylsulfonylamino group, arylsulfonylamino group, alkylthio group, arylthio group, hetero-ring thio group, alkoxycarbonyl group, or carbamoyl group, "w" represents an integer of from 1 to 4 wherein several $R_{114}$ groups in the number "w" may be the same or different; "x" represents an integer of from 0 to 6. wherein several $R_{115}$ groups in the number "x" may be the same or different, $B_{116}$, $R_{117}$, $R_{118}$, and $R_{119}$ independently represent an alkyl group or aryl group, $R_{120}$ and $R_{121}$ independently represent an alkyl group, aryl group, hetero-ring group, cyano group, alkylsulfonyl group, arylsulfonyl group, alkoxycarbonyl group, or carbamoyl group; $R_{122}$ represents a hydrogen atom, alkyl group, aryl group, hetero-ring group, acylamino group, alkylsulfonylamino group, or arylsulfonylamino group, $R_{123}$ and $R_{124}$ independently represent an alkyl group, aryl group, hetero-ring group, cyano group, alkylsulfonyl group, arylsulfonyl group, alkoxycarbonyl group, or carbamoyl group; $Z_4$ represents a non-metal atomic group forming a 5-membered or 6-membered ring, together with the two nitrogen atoms and one carbon atom, $R_{125}$ represents an alkyl group, aryl group, alkoxy group, amino group, acylamino group, alkylsulfonylamino group, arylsulfonylamino group, alkylthio group, arylthio group, acyl group, alkoxycarbonyl group, or carbamoyl group; "y" represents an integer of from 0 to 2, when $Z_4$ forms a 5-membered ring; and "y" represents an integer of from 0 to 3, when $Z_4$ forms a 6-membered ring, and $R_{126}$ represents an alkylgrou a 1 roup,cyano group or alkoxy carbonyl group;

and wherein $R_{101}$ to $R_{126}$ in formulas (B-1) to (B-12) may have additional substituents; and, with the proviso "A" and "B" are free of sulfo, carboxyl and quatemary ammonium groups.

9. The method according to claim 8, wherein the structure of the azo dye is represented by any one of DS-1 to DS-9:

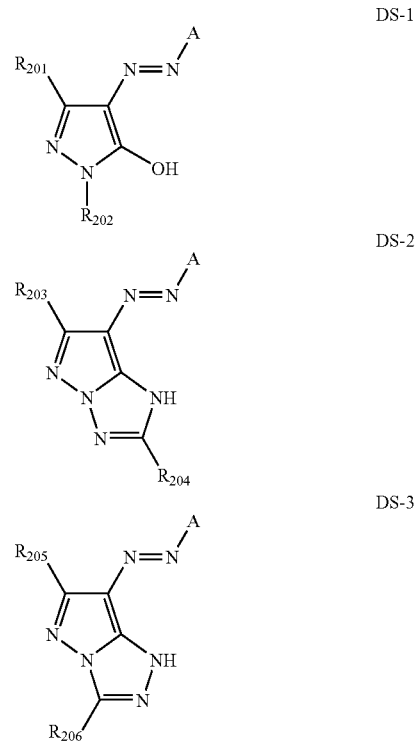

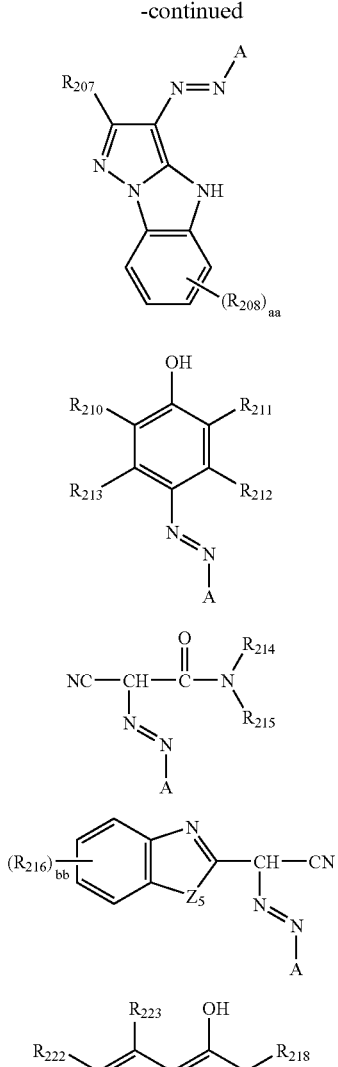

wherein "A" has the same meaning as defined in claim 1;

$R_{201}$ represents a hydrogen atom, alkyl group, aryl group, alkoxy group, amino group (including anilino group), alkoxycarbonyl group, cyano group, acylamino group, or carbamoyl group; $R_{202}$ represents a hydrogen atom, alkyl group, aryl group, or hetero-ring group;

$R_{203}$, $R_{205}$ and $R_{207}$ represent a hydrogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, or carbamoyl group; $R_2O4$ represents an alkyl group, aryl group, or hetero-ring group;

$R_{206}$ represents an alkyl group, aryl group, hetero-ring group, alkylthio group, arylthio group, alkoxycarbonyl group, or carbamoyl group;

$R_{208}$ represents a halogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, alkoxycarbonyl group, or carbamoyl group; "aa" represents an integer of from 0 to 4, provided that aa is 2 to 4, the $R_{208}$ groups may be the same or different;

$R_{210}$ represents a hydrogen atom, halogen atom, alkyl group, aryl group, acylamino group, alkoxycarbonyl group, aminocarbonylamino group, alkylsulfonylamino group, arylsulfonylamino group, alkoxycarbonylamino group, or carbamoyl group; $R_{211}$ represents a halogen atom, alkyl group, aryl group, acylamino group, alkoxycarbonyl group, aminocarbonylamino group, alkylsulfonylamino group, arylsulfonylamino group, alkoxycarbonylamino group, or carbamoyl group; $R_{212}$ and $R_{213}$ independently represent a hydrogen atom, halogen atom, alkyl group, alkoxy group, or acylamino group;

$R_{214}$ and $R_{215}$ independently represent a hydrogen atom, alkyl group, aryl group, or hetero-ring group;

$R_{216}$ represents a halogen atom, alkyl group, aryl group, hetero-ring group, cyano group, alkoxy group, amino group (including anilino group), acylamino group, alkylsulfonylamino group, arylsulfonylamino group, alkylthio group, arylthio group, sulfamoyl group, alkylsulfonyl group, or carbamoyl group; $Z_5$ represents an oxygen atom, sulfur atom, or —N($R_{217}$)—, where $R_{217}$ represents a hydrogen atom, alkyl group, aryl group, or hetero-ring group; "bb" represents an integer of from 0 to 4; provided that if "bb" is a plural number, the Rn6 groups in the number "bb" may be the same or different;

$R_{218}$ represents a hydrogen atom, halogen atom, alkyl group, aryl group, acylamino group, alkylsulfonylamino group, arylsulfonylamino group, alkoxycarbonylamino group, aminocarbonylamino group, carbamoyl group, or sulfamoyl group; $R_{220}$ and $R_{223}$ independently represent a hydrogen atom, halogen atom, acylamino group, alkoxycarbonylamino group, aminocarbonylamino group, alkylsulfonylamino group, or arylsulfonylamino group; $R_{219}$, $R_{221}$, and $R_{222}$ independently represent a hydrogen atom, chlorine atom, bromine atom, alkyl group, or acylamino group; and $R_{224}$ represents an alkyl group, aryl group, cyano group or alkoxycarbonyl group wherein $R_{201}$ to $R_{224}$ in formulas DS-1 to DS-9 may have additional substituents.

10. The method according to claim 8, wherein the azo dye of formula (1) is present in an amount of from about 0.000 1 to 20 % by weight, based on the whole composition.

11. The method according to claim 8, further comprising at least one direct dye other than the azo dye of general formula (1) andlor at least one oxidative dye.

12. The method according to claim 11, wherein the total amount of the dyes present in said composition is from about 0.001% to 20 % by weight, based on the whole composition.

13. The method according to claim 8, further comprising an alkaline agent in an amount of from about 0.01% to 20 % by weight, based on the whole composition.

14. The method according to claim 8, being a one part composition, a two part composition or a three part composition, wherein the two part composition comprises a first part containing an alkaline agent and a second part containing an oxidative agent, and wherein the three part composition contains the first and second parts and additionally a third part containing a powdery oxidizing agent, wherein in each of the said composition the direct dye having formula (1) is contained in either one of the respective parts or in each part.

* * * * *